US009618524B2

(12) United States Patent
Madasamy

(10) Patent No.: US 9,618,524 B2
(45) Date of Patent: *Apr. 11, 2017

(54) METHOD, COMPOSITION, ISOLATION AND IDENTIFICATION OF A PLAQUE PARTICLE AND RELATED BIOMARKER

(71) Applicant: Shanmugavel Madasamy, Cupertino, CA (US)

(72) Inventor: Shanmugavel Madasamy, Cupertino, CA (US)

(73) Assignee: Plaxgen Inc., Fremont, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 14/225,788

(22) Filed: Mar. 26, 2014

(65) Prior Publication Data
US 2015/0276771 A1 Oct. 1, 2015

Related U.S. Application Data

(63) Continuation-in-part of application No. PCT/US2012/066412, filed on Nov. 21, 2012.

(51) Int. Cl.
*A61K 35/00* (2006.01)
*C07K 2/00* (2006.01)
*G01N 1/28* (2006.01)
*G01N 33/92* (2006.01)
*G01N 33/68* (2006.01)

(52) U.S. Cl.
CPC ......... *G01N 33/92* (2013.01); *G01N 33/6848* (2013.01); *G01N 2333/4709* (2013.01); *G01N 2405/04* (2013.01); *G01N 2560/00* (2013.01); *G01N 2570/00* (2013.01)

(58) Field of Classification Search
None
See application file for complete search history.

(56) References Cited

PUBLICATIONS

Santos, A. N. et al., Detection of amyloid-β oligomers in human cerebrospinal fluid by flow cytometry and fluorescence resonance energy transfer. J. Alzheimers Dis. 11 (2007) 117-125.*
Mayr et al., Proteomics, Metabolomics, and Immunomics on Microparticles Derived From Human Atherosclerotic Plaques. Circ Cardiovasc Genet. 2009;2:379-388; originally published online May 14, 2009.*

* cited by examiner

*Primary Examiner* — Jeffrey Stucker
*Assistant Examiner* — Aurora M Fontainhas
(74) *Attorney, Agent, or Firm* — Geeta Kadambi Riddhi IP LLC

(57) ABSTRACT

The disclosure relates to an in vitro technology of detecting presence of a plaque particle, isolating the plaque particle followed by its composition analysis in several diseases states or before the disease sets in. A mechanism and a process leading to plaque formation, identifying a component in the mechanism of plaque formation, an identification of a biomarker for diagnosis/early diagnosis of plaque associated disease is described. A method of screening a candidate agent as an anti-plaque agent using flow cytometer, mass spectrometer and specific biomarkers is performed. Provided also are kits for use in practicing embodiment of the methods. A plaqueproteome database is also generated with novel protein sequences for diagnosis and specific antibodies for specific proteins are also disclosed.

3 Claims, 17 Drawing Sheets

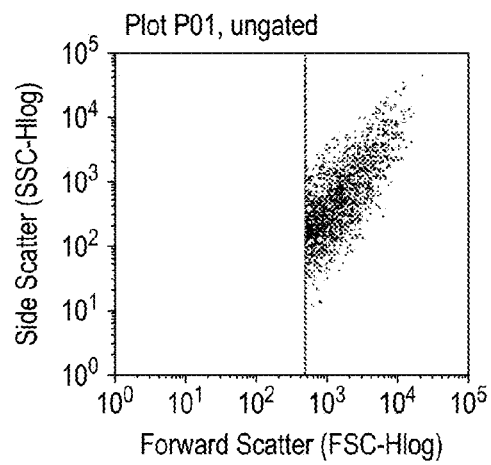
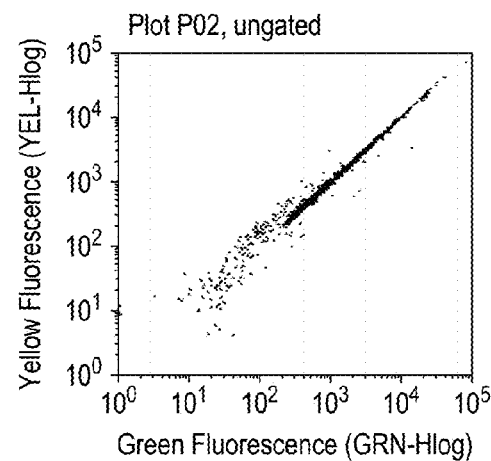
*FIG. 3A*  *FIG. 3B*
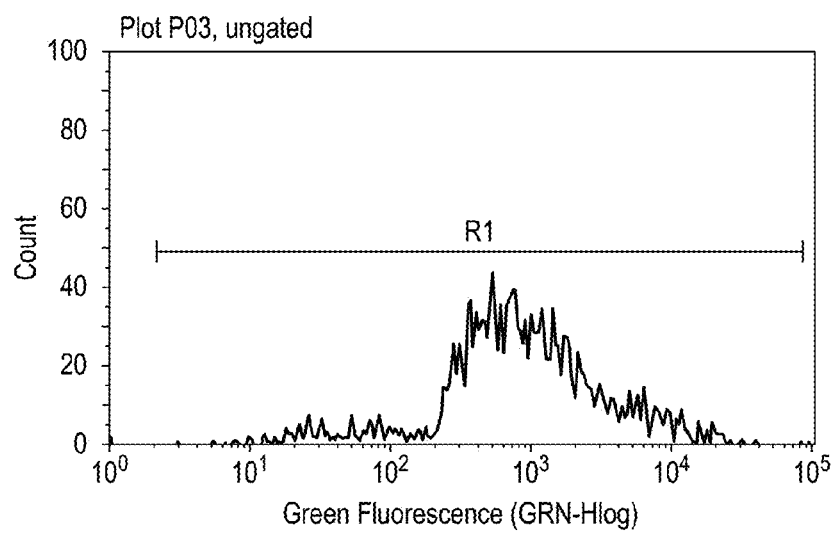
*FIG. 3C*

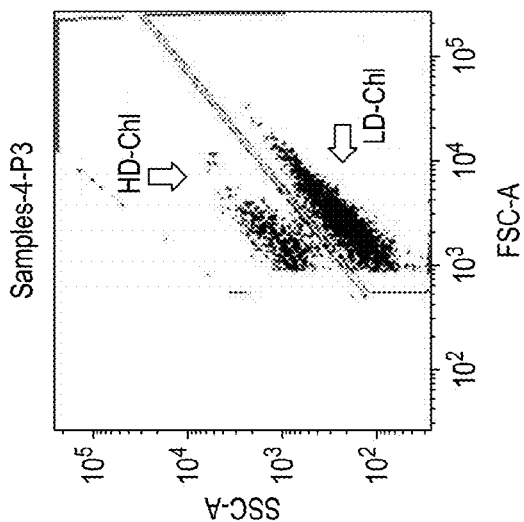
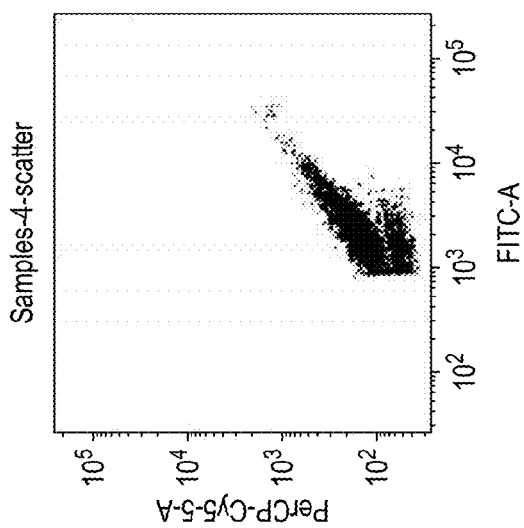
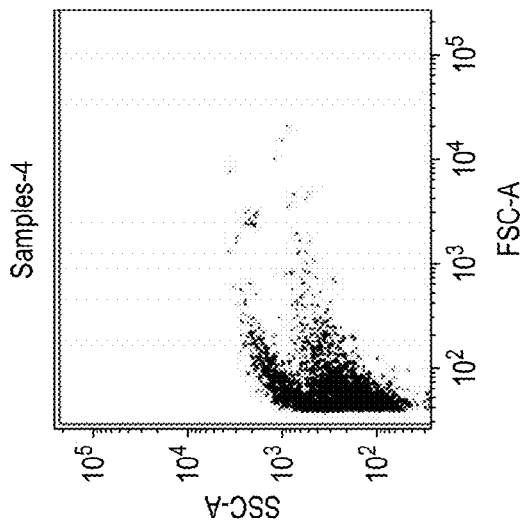
FIG. 7C
FIG. 7B
FIG. 7A

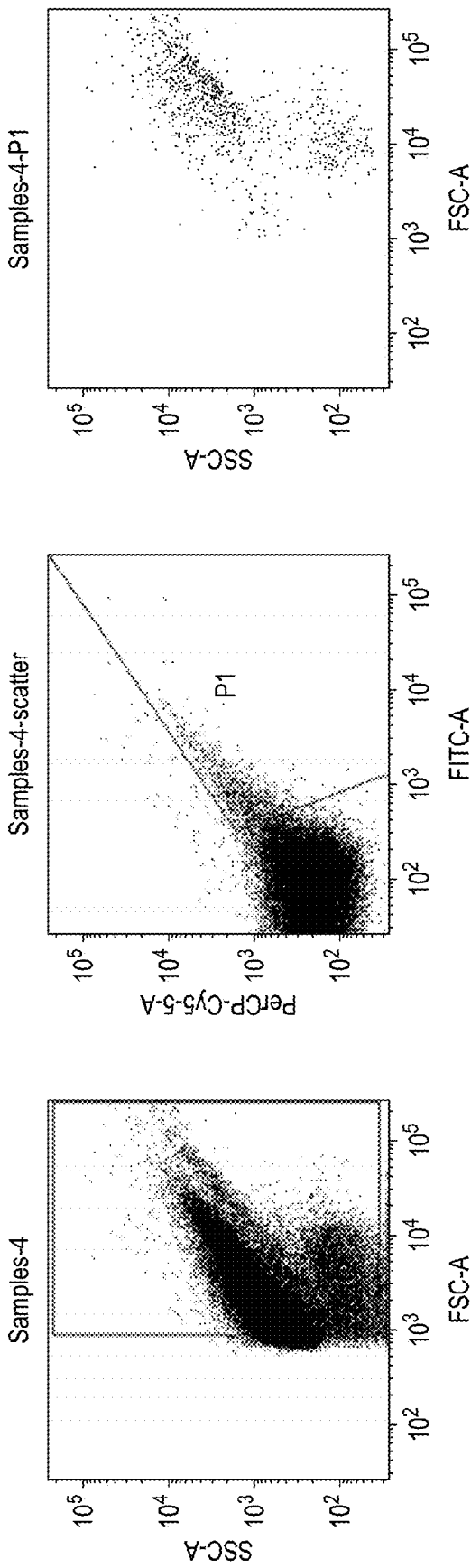

SEQUENCE LISTING

```
<160> NUMBER OF SEQ ID NOS: 21

<210> SEQ ID NO 1
<211> LENGTH: 42
<212> TYPE: PRT
<213> ORGANISM: Human

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 28
<212> TYPE: PRT
<213> ORGANISM: Human

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

<210> SEQ ID NO 3
<211> LENGTH: 17
<212> TYPE: PRT
```

<213> ORGANISM: Human

<400> SEQUENCE: 3

Asp Ala Glu Phe Arg His Asp Ser Gly Tyr Glu Val His His Gln Lys
1               5                   10                  15

Leu

<210> SEQ ID NO 4
<211> LENGTH: 14
<212> TYPE: PRT
<213> ORGANISM: Human

<400> SEQUENCE: 4

Glu Asp Val Gly Ser Asn Lys Gly Ala Ile Ile Gly Leu Met
1               5                   10

<210> SEQ ID NO 5
<211> LENGTH: 42
<212> TYPE: PRT
<213> ORGANISM: Human

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Cys Asn Lys Gly Ala Ile Ile
                20                  25                  30

Gly Leu Met Val Gly Gly Val Val Ile Ala
            35                  40

<210> SEQ ID NO 6
<211> LENGTH: 42
<212> TYPE: PRT
<213> ORGANISM: HUMAN

<400> SEQUENCE: 6

Asp Ala Glu Phe Arg His Asp Ser Gly Tyr Glu Val His His Gln Lys
1               5                   10                  15

Leu Val Phe Phe Ala Val Asp Val Gly Ser Asn Lys Gly Ala Ile Ile
                20                  25                  30

Gly Leu Met Val Gly Gly Val Val Ile Ala
            35                  40

<210> SEQ ID NO 7
<211> LENGTH: 42
<212> TYPE: PRT
<213> ORGANISM: Human

<400> SEQUENCE: 7

Asp Ala Glu Phe Arg His Asp Ser Gly Tyr Glu Val His His Gln Lys
1               5                   10                  15

Leu Val Phe Phe Ala Glu Asp Val Gly Ser Ala Lys Gly Ala Ile Ile
                20                  25                  30

Gly Leu Met Val Gly Gly Val Val Ile Ala
            35                  40

<210> SEQ ID NO 8
<211> LENGTH: 24
<212> TYPE: PRT
<213> ORGANISM: Human

<400> SEQUENCE: 8

```
Trp Glu Arg Pro Phe Glu Val Lys Asp Thr Glu Glu Asp Phe His
1               5                   10                  15

Val Asp Gln Val Thr Thr Val Lys
                20
```

<210> SEQ ID NO 9
<211> LENGTH: 18
<212> TYPE: PRT
<213> ORGANISM: Human

<400> SEQUENCE: 9

```
Val Phe Ser Asn Gly Ala Asp Leu Ser Gly Val Thr Glu Glu Ala Pro
1               5                   10                  15

Leu Lys
```

<210> SEQ ID NO 10
<211> LENGTH: 105
<212> TYPE: PRT
<213> ORGANISM: Human

<400> SEQUENCE: 10

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
                20                  25                  30

Phe Tyr Pro Gly Ala Val Thr Val Ala Trp Lys Ala Asp Gly Ser Pro
            35                  40                  45

Val Lys Val Gly Val Glu Thr Thr Lys Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Val Glu
                85                  90                  95

Lys Thr Val Ala Pro Ala Glu Cys Ser
            100                 105
```

<210> SEQ ID NO 11
<211> LENGTH: 115
<212> TYPE: PRT
<213> ORGANISM: Human

<400> SEQUENCE: 11

```
Met Glu Ala Pro Ala Gln Leu Leu Phe Leu Leu Leu Trp Leu Pro Asp
1               5                   10                  15

Thr Thr Arg Glu Ile Val Met Thr Gln Ser Pro Pro Thr Leu Ser Leu
                20                  25                  30

Ser Pro Gly Glu Arg Val Thr Leu Ser Cys Arg Ala Ser Gln Ser Val
            35                  40                  45

Ser Ser Ser Tyr Leu Thr Trp Tyr Gln Gln Lys Pro Gly Gln Ala Pro
50                  55                  60

Arg Leu Leu Ile Tyr Gly Ala Ser Thr Arg Ala Thr Ser Ile Pro Ala
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Val Tyr Tyr Cys Gln Gln Asp His
            100                 105                 110

Asn Leu Pro
        115
```

<210> SEQ ID NO 12
<211> LENGTH: 117
<212> TYPE: PRT
<213> ORGANISM: Human

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Val
            20                  25                  30

Leu Ser Ser Trp Val Arg Gln Ala Pro Gly Lys Gly Leu Glu Trp Val
        35                  40                  45

Ser Gly Arg Leu Asn Ala Ser Ser Asn Leu His Phe Ala Val Ser Ala
    50                  55                  60

Gln Gly Arg Phe Thr Ile Ser Arg Asn Asp Ser Lys Asn Thr Leu Tyr
65                  70                  75                  80

Leu Gln Met Leu Ser Leu Gln Ala Glx Asx Thr Ala Leu Tyr Tyr Cys
                85                  90                  95

Ala Arg Leu Leu Ser Val Tyr Ala Val Ala Phe Asp Val Trp Gly Gln
            100                 105                 110

Gly Thr Lys Val Ser
        115

<210> SEQ ID NO 13
<211> LENGTH: 326
<212> TYPE: PRT
<213> ORGANISM: Human

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

```
Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                    245                 250                 255

Ser Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 14
<211> LENGTH: 330
<212> TYPE: PRT
<213> ORGANISM: Human

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
                    245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 109
<212> TYPE: PRT
<213> ORGANISM: Human

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ala Leu Leu Ser Arg Gly
            20                  25                  30

Tyr Leu Ala Trp Tyr Gln Gln Lys Pro Gly Gln Ala Pro Arg Leu Leu
        35                  40                  45

Met Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Ser Phe Gly Gln Gly Thr Lys Val Glu Ile Lys Arg
            100                 105

<210> SEQ ID NO 16
<211> LENGTH: 108
<212> TYPE: PRT
<213> ORGANISM: Human

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
            20                  25                  30

Phe Leu Ala Trp Tyr Gln Gln Lys Pro Gly Gln Ala Pro Arg Leu Leu
        35                  40                  45

Ile Tyr Val Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ser Thr Phe Gly Gln Gly Thr Val Glu Leu Lys Arg
            100                 105

<210> SEQ ID NO 17
<211> LENGTH: 108
<212> TYPE: PRT
```

```
<213> ORGANISM: Human

<400> SEQUENCE: 17

Asp Val Gln Met Thr Gln Ser Pro Ser Ser Leu Ser Ala Val Gly Asp
1               5                   10                  15

Arg Val Ile Ile Thr Cys Arg Ala Ser Gln Ser Val Asp Tyr Leu
            20                  25                  30

Asn Trp Tyr Gln Gln Lys Pro Gly Lys Ala Pro Lys Leu Leu Ile Phe
        35                  40                  45

Asp Thr Ser Asn Leu Gln Ser Gly Val Pro Ser Arg Phe Ser Gly Gly
    50                  55                  60

Arg Ser Gly Thr Asp Phe Thr Leu Thr Ile Ser Ser Leu Gln Pro Asp
65                  70                  75                  80

Asp Phe Ala Thr Tyr Tyr Cys Gln Gln Ser Tyr Thr Asn Pro Glu Val
                85                  90                  95

Thr Phe Gly Gly Gly Thr Thr Val Asp Ile Lys Arg
            100                 105

<210> SEQ ID NO 18
<211> LENGTH: 110
<212> TYPE: PRT
<213> ORGANISM: Human

<400> SEQUENCE: 18

Asp Val Val Met Thr Gln Ser Pro Leu Phe Pro Val Thr Leu Gly Glu
1               5                   10                  15

Pro Ala Ser Ile Gln Cys Arg Ser Ser Gln Ser Leu Val Tyr Asx Gly
            20                  25                  30

Asx Thr Tyr Leu Asx Trp Tyr Leu Gln Lys Pro Gly Ser Pro Glu Leu
        35                  40                  45

Leu Ile Tyr Leu Ser Ser Tyr Arg Asp Ser Gly Val Pro Asp Arg Leu
    50                  55                  60

Ser Asp Ser Gly Ser Gly Thr Asp Phe Thr Leu Lys Ile Thr Arg Val
65                  70                  75                  80

Gln Ala Glu Asp Val Gly Val Tyr Tyr Cys Met Gln Ala Thr Glx Ser
                85                  90                  95

Pro Tyr Thr Phe Gly Gln Gly Thr Lys Leu Glx Ile Lys Arg
            100                 105                 110

<210> SEQ ID NO 19
<211> LENGTH: 108
<212> TYPE: PRT
<213> ORGANISM: Human

<400> SEQUENCE: 19

Asp Ile Gln Met Thr Gln Ser Pro Ser Thr Leu Ser Ala Ser Val Gly
1               5                   10                  15

Asp Arg Val Ala Ile Arg Thr Cys Arg Ala Ser Gln Asn Ile Ser Ser
            20                  25                  30

Trp Leu Ala Trp Tyr Gln Gln Lys Pro Gly Lys Ala Pro Lys Val Leu
        35                  40                  45

Ile Tyr Lys Ser Ser Ser Leu Glu Ser Gly Val Pro Ser Arg Phe Ser
    50                  55                  60

Gly Ser Gly Ser Gly Thr Asp Thr Asp Phe Thr Leu Thr Ile Ser Ser
65                  70                  75                  80

Leu Glx Pro Asx Asx Phe Ala Thr Tyr Tyr Cys Gln Gln Tyr Asn Thr
                85                  90                  95
```

```
Phe Phe Thr Gly Pro Gly Thr Val Asp Ile Lys Arg
                100             105

<210> SEQ ID NO 20
<211> LENGTH: 117
<212> TYPE: PRT
<213> ORGANISM: Human

<400> SEQUENCE: 20

Glu Val Gln Leu Leu Glu Ser Gly Gly Leu Val Gln Pro Gly Gly
1               5                   10                  15

Ser Leu Arg Leu Ser Cys Ala Ala Ser Gly Phe Ser Phe Ser Thr Asp
            20                  25                  30

Ala Met Tyr Trp Val Arg Gln Ala Pro Gly Lys Gly Leu Glu Trp Val
        35                  40                  45

Ala Trp Lys Tyr Gln Glu Ala Ser Asn Ser His Phe Ala Asp Thr Val
    50                  55                  60

Asn Arg Gly Phe Thr Ile Ser Arg Asn Asp Ser Lys Asn Thr Leu Tyr
65                  70                  75                  80

Leu Gln Met Asn Arg Leu Glu Ala Glx Asx Thr Ala Val Tyr Tyr Cys
                85                  90                  95

Ala Arg Phe Arg Gln Pro Phe Val Gln Phe Phe Asp Val Phe Gly Gln
                100             105                 110

Gly Thr Leu Val Thr
            115

<210> SEQ ID NO 21
<211> LENGTH: 122
<212> TYPE: PRT
<213> ORGANISM: Human

<400> SEQUENCE: 21

Gln Val Lys Leu Val Gln Ala Gly Gly Val Val Gln Pro Gly Arg
1               5                   10                  15

Ser Leu Arg Leu Ser Cys Ile Ala Ser Gly Phe Thr Phe Ser Asn His
            20                  25                  30

Gly Met His Trp Val Arg Gln Ala Pro Gly Lys Gly Leu Glu Trp Val
        35                  40                  45

Ala Val Ile Trp Tyr Asn Gly Ser Arg Thr Tyr Tyr Gly Asp Ser Val
    50                  55                  60

Lys Gly Arg Phe Thr Ile Ser Arg Asn Asp Asn Ser Lys Arg Thr Leu
65                  70                  75                  80

Tyr Met Glx Met Asn Ser Leu Arg Thr Glu Asp Thr Ala Val Tyr Tyr
                85                  90                  95

Cys Ala Arg Asp Pro Asp Ile Leu Thr Ala Phe Ser Phe Asp Tyr Trp
                100             105                 110

Gly Gln Gly Val Leu Val Thr Val Ser Ser
            115                 120
```

METHOD, COMPOSITION, ISOLATION AND IDENTIFICATION OF A PLAQUE PARTICLE AND RELATED BIOMARKER

CROSS-REFERENCE TO RELATED APPLICATIONS

This application claims priority from and is a continuation-in-part (CIP) of PCT/US2012/066412 filed on Nov. 21, 2012 which is incorporated herein by reference.

FIELD OF TECHNOLOGY

The present application relates generally to methods and compositions relating to formation of multiple types of plaque particles in biological samples and their detection, isolation and biomarkers identification. More specifically, the present application relates to use of Flow cytometer and Mass spectroscopy for isolation and identification of molecules that contribute to formation of plaque particles.

BACKGROUND

Plaque development is a complex pathogenic process occurring mainly due to abnormal deposition of molecules such as cholesterol, lipids, amyloid peptides, metals and metabolites in blood vessels (Viola M et al, 2013; Thal D R et al, 2008). These molecules, while existing in the soluble form, are involved in the normal functions of key biochemical pathways, however, their abnormal metabolism is implicated to origin of many vascular and neurodegenerative disorders (Wirth M et al, 2013; Brown W R, 2011). More specifically, transformation of cholesterol and amyloid peptides from their initial soluble form into oligomers or aggregates and finally into insoluble plaque particles is the primary cause in the development of atherosclerotic and amyloid plaques.

The plaque forming aggregates once formed inappropriately interact with a wide range of bio-molecules present in the surrounding extracellular or intracellular spaces. Endogenous physiological pathways such as proteolytic and immune system play critical role in the clearance of the aggregates. However, under abnormal conditions defective clearance of the plaque aggregates or oligomers leads to their progressive accumulation in the coronary and cerebrovascular regions of blood vessels ultimately leading to fatal symptomatic events such as Myocardial Infarction and dementia (Sultan M, 2014; Grimm Mo. et al. 2013).

Although, the major components present in the atherosclerotic and amyloid plaques have been identified as the underlying biochemical mechanism of plaque assembly process, however it is not completely understood. This is mainly due to the fact that in vivo plaque development is a slow pathological process covering a larger window period of time spanning years to decades since the early asymptomatic stage to occurrence of symptomatic events.

Currently, autopsy and biopsy samples are used to examine plaque composition with limited success and often these samples are contaminated with host cell and tissue contributing to misleading scientific observations leading to a gap in diagnosis and treatment.

SUMMARY

The present disclosure relates to an in vitro technology of detecting presence of a plaque particle, isolating the plaque particle followed by its composition analysis. Further, the present application also relate to understanding a mechanism of or a process leading to plaque formation, identifying a component in the mechanism of plaque formation and a method of screening a candidate agent as an anti-plaque agent. The present disclosure also relates to identifying a bio-marker of plaque formation leading to early diagnosis or diagnosis of plaque associated disease. More specifically, the present disclosure relates to an in vitro technology of isolating at least one plaque particle or plurality of plaque particles using a flow cytometer, separating the plaque particle based on different physical parameters; analyzing the particle through Mass Spectroscopy and analyzing a bio-molecule or plurality of bio-molecules present in the plaque particle followed by identifying a bio-marker. Also provided are kits for use in practicing embodiments of the methods.

In one embodiment, the present application relates to a method, comprising: preparing a plaque aggregate or a plaque oligomer in vitro, wherein the plaque aggregate or a plaque oligomer is linked to a detectable signal; contacting a biological sample from a subject with the plaque aggregate or the plaque oligomer to form an insoluble plaque particle; isolating the plaque particle; and analyzing a bio-molecule in the plaque particle to identify composition of plaque particle. In another embodiment, the present application relates to a method, comprising: preparing a plaque aggregate or a plaque oligomer in vitro, wherein the plaque aggregate or the plaque oligomer is linked to a detectable signal; contacting a biological sample from a subject with the plaque aggregate or the plaque oligomer to form an insoluble plaque particle, wherein the subject is previously diagnosed with a plaque associated disease; isolating the plaque particle using a flow cytometer; and analyzing a bio-molecule in the plaque particle using mass spectroscopy to identify composition of plaque particle.

In one embodiment, the present application relates to a method, comprising: preparing a plaque aggregate or a plaque oligomer in vitro, wherein the plaque aggregate or the plaque oligomer is linked to a detectable signal; contacting a biological sample from a subject with the plaque aggregate or the plaque oligomer; isolating a plurality of plaque particles; and analyzing a plurality of bio-molecules in the plaque particles to identify a biomarker or a plurality of biomarkers in the biological sample. In some embodiments, the contacting is with at least one plaque aggregate or at least one plaque oligomer whereas in another embodiment, the contacting is with a plurality of plaque aggregates or a plurality of plaque oligomers.

In most embodiments, analysis of at least one bio-molecule or a plurality of bio-molecules as disclosed may lead to an identification of a biomarker for early diagnosis of plaque associated disease.

In one embodiment, a biological sample is a biological fluid wherein the biological fluid is selected from the group consisting of blood, plasma, serum, cerebral spinal fluid, urine and saliva. In another embodiment, a biological fluid may be a clinical or a non-clinical fluid sample.

In one embodiment, the contacting of biological sample is with at least one plaque aggregate, oligomer or a self-formed plaque particle wherein the contacting of biological sample with at-least one plaque aggregate, oligomer or a self-formed plaque particle triggers a mechanism leading to a formation of at-least one plaque particle. The plaque particle as formed in vitro resembles a plaque associated with Atherosclerosis, Alzheimer's disease (AD), Autism, Parkinson's disease (PD), Multiple Sclerosis (MS), Osteoarthritis, Mad Cow Sponsiform (MCS), Type II diabetes, Dementia, Systemic Amyloidosis (SA), Dialysis-related Amyloidosis, Huntington disease, Levy bodies, Lysozyme myloidosis, Insulin-related Amyloidosis, Amyotrophic Lateral Sclerosis (ALS) and/or other plaque-related and associated disorders.

The subject as disclosed in the present application may be a person or a patient diagnosed previously with a plaque associated disease which may include but not limited to Atherosclerosis, AD, Autism, PD, MS, Osteoarthritis, MCS, Type II diabetes, Dementia, SA, Dialysis-related Amyloidosis, Lysozyme Amyloidosis, Huntington disease, Levy bodies insulin-related Amyloidosis, ALS and/or other plaque-related and associated disorders. In some embodiments, the subject may be a person or a patient at risk of having, suspected of having or a family history of having plaque associated disease. In some embodiments, the method further comprises diagnosing or stratifying subjects based on plaque particle formation, plaque particle subtypes, plaque particle images, plaque particle count, or plaque particle profile.

In some embodiments, the detecting label may be a fluorescent, chemiluminscent, radio-labeled, enzymatic or an antibody labeled with fluorescence or metal and thus may be detected using known assays. In a preferred embodiment, the detectable label may be a fluorescent label, thus detecting at least one fluorescent labeled plaque aggregate, plurality of plaque aggregates or a pair of plaque aggregates labeled with different fluorophores using fluorescence resonance energy transfer (FRET).

In one embodiment, at least one plaque aggregate, plaque oligomer or self-formed plaque particle comprises one or more of the following: protein, protein derivative, cholesterol, cholesterol derivative, lipid, lipid derivative, Abeta-42, Abeta derivatives, Synuclein, prion, Amylin, Tau, Tau derivative, phospholipids, cholesterol crystals, Serum Amyloid A, Beta Microglobulin, lysozyme, insulin, or super dioxide dismutase, and calcium-phosphate (CP).

In one embodiment, the present disclosure further relates to a method of screening a candidate agent as an anti-plaque agent. The candidate agent may act to prevent, inhibit or stimulate the in-vitro formation of the plaque particle. The method of screening a candidate agent as disclosed, comprises: preparing a plaque aggregate or a plaque oligomer in vitro, wherein the plaque aggregate or the plaque oligomer is linked to a detectable signal; contacting a biological sample from a subject with the plaque aggregate or the plaque oligomer; adding the candidate agent or libraries of candidate agents; isolating the plaque particle; and analyzing a bio-molecule in the plaque particle and comparing it with a bio-molecule identified in the plaque particle isolated from biological sample not in contact with the candidate agent to screen the candidate agent as an anti-plaque agent. The candidate agent may be added before the contacting or after the contacting with the biological sample. In most embodiments, the biological sample where the candidate agent is not added before and after the contacting is considered as a control sample for screening methods. A candidate agent as disclosed, may include but not limited to a chemical compound, a small molecule, a therapeutic drug, a biological molecule, a natural compound, a natural or a synthetic oligomer, a ligand, a protein, an antibody and/or other component capable of binding the plaque aggregate, plaque oligomer, self-formed plaque particle or plaque particle in the presence or absence of biological sample, preventing their assembly, disassembling these aggregates, oligomers, self-formed plaque particles or plaque particles once already formed, or reducing their pathogenic properties. The screening method will further identify candidate agent for their potential as therapeutics for diagnosing, preventing, treating, and/or curing plaque related diseases.

Thus, in one embodiment, the disclosure relates to a method of screening a candidate agent comprising: preparing at least one plaque aggregate or a plaque oligomer in vitro wherein the at least one plaque aggregate or plaque oligomer is linked to a detectable label; culturing mammalian cells with the at least one plaque aggregate or plaque oligomer wherein the mammalian cells express morphologic changes, pathological symptoms, cell adhesion molecules, cytokines and or apoptosis, inflammation; contacting the mammalian cells at least one candidate agent; and then identifying candidate agent that prevent or lessen the formation of pathological symptoms or morphological changes in the cells.

In one embodiment, a mechanism of plaque formation will also be evaluated by disclosed technology. The mechanism may be delineated by the bio-molecule analyzed and quantitated before and after the formation of plaque aggregates. In one embodiment, the present disclosure relates to a method, comprising: preparing a plaque aggregate or a plaque oligomer in vitro, wherein the plaque aggregate or the plaque oligomer is linked to a detectable signal; analyzing a bio-molecule in a biological sample from a subject; contacting the biological sample with the plaque aggregate or the plaque oligomer; detecting the plaque particle; isolating the plaque particle; analyzing a bio-molecule in the plaque particle; and comparing the biomolecule analyzed before and after the contacting of the biological sample to delineate a mechanism of plaque formation. In another embodiment, the method as disclosed can further be elaborated to identify a biomarker or plurality of biomarkers for diagnosis and early diagnosis of plaque related disease. The bio-molecules as identified may then be correlated to the biochemical pathways indicating a mechanism of plaque formation.

In one embodiment, a method to prepare a plaque forming oligomer or aggregate is disclosed. In another embodiment, a plaque forming cholesterol, phospholipid and amyloid oligomer or aggregate is disclosed. The plaque forming oligomer or aggregate as synthesized may then be used for in vitro plaque formation as described.

In one embodiment, the present disclosure relates to a method of sorting and isolating a plaque particle synthesized in the biological sample such as a bio-fluid. In one embodiment, the present disclosure relates to a method of sorting and isolating the plaque particle synthesized in the bio-fluid using a flow cytometer. The method as disclosed comprise of preparing a plaque aggregate or a plaque oligomer in vitro, wherein the plaque aggregate or the plaque oligomer is linked to a detectable signal; preparing a plaque aggregate in vitro using at least one of a plaque biomarker, plaque oligomer, plaque antibody and a combination thereof; contacting the biological sample with the plaque aggregate or the plaque oligomer; detecting a formation of the aggregate via the detectable signal; introducing the aggregate to a flow cytometer; performing a dot blot analysis; separating the aggregate particle; and collecting the separated particles for further composition analysis. The aggregate particles may be separated based on differences in density, mass or complex formation.

In one embodiment, the present disclosure relates to a method of processing an isolated plaque particle for its composition analysis which may be a proteomics, lipidomics, glycomics and metabolomics based composition analysis. In most embodiments, the present disclosure relates to a method of processing an isolated plaque particle for mass spectroscopy based proteomics, lipidomics, glycomics and metabolomics analyses.

In another embodiment, the present disclosure relates to a kit for preparation of a plaque aggregate or a plaque oligomer whereas in another embodiment, the present disclosure relates to a kit for segregating and isolating plaque particle. In another embodiment, the present disclosure also relate to a kit comprising: collecting a biological sample from a subject, contacting it to a plaque oligomer; estimating a plaque particle; segregating and isolating the plaque particle and analyzing the biomarker. In most embodiments, the present disclosure relates to a kit for estimating a biomarker for plaque related diseases in a biological sample from a subject which may be a person or a patient at risk of having, suspected of having or a family history of having plaque associated disease. In one embodiment, a plaqueproteome database is compiled. In another embodiment, antibody leads that may be used as a plaque oligomer, plaque aggregate is disclosed.

The method, composition, isolation and identification of a plaque particle and related biomarker disclosed herein may be implemented in any means for achieving various aspects, and may be executed in a form suitable for the mammal and or other vertebrate animals. Other features will be apparent from the accompanying drawings and from the detailed description that follows.

BRIEF DESCRIPTION OF THE DRAWINGS

Example embodiment are illustrated by way of example and no limitation in the accompanying Figures and tables, like references indicate similar elements and in which:

FIGS. 3A, 3B and 3C represents a flow cytometer based detection of Abeta-28 plaque particles.

FIGS. 7A, 7B and 7C represents a flow cytometer based sorting and isolation of high density and low density cholesterol plaque particles.

FIGS. 9A, 9B and 9C represents a flow cytometer based sorting and isolation of Abeta-28 plaque particles.

DETAILED DESCRIPTION

Figure 1:
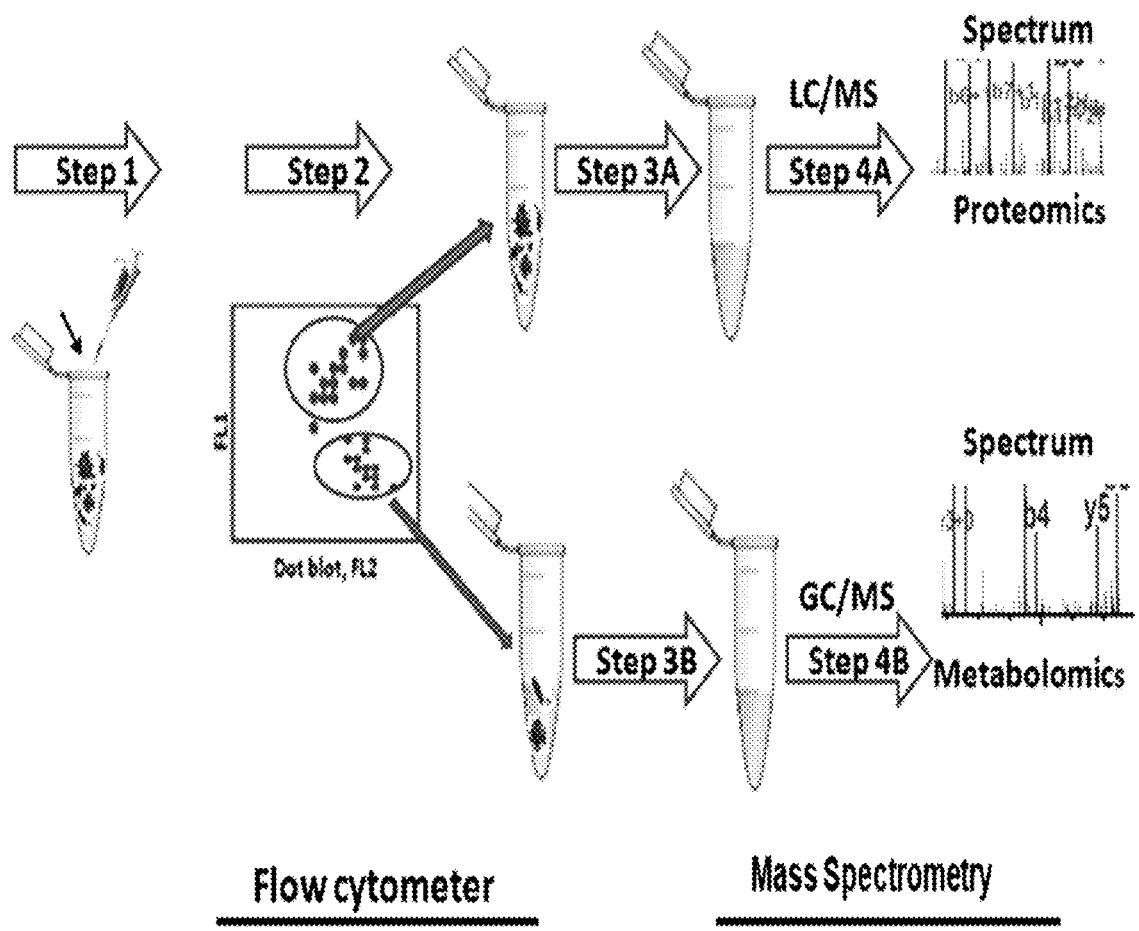
FIG. 1 represents a schematic of the flow cytometer and Mass spectroscopy based detection, sorting and biomarkers identification in plaque particles.

Several methods, composition, isolation techniques, kit, and identification procedures of a plaque particle, related biomarkers and plaque specific antibody leads are discussed in the instant disclosure. Although the present embodiment have been described with reference to specific example embodiment, it will be evident that various modifications and changes may be made to these embodiment without departing from the broader spirit and scope of the various embodiment. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification.

There is currently a lack of in vitro technology to efficiently isolate plaque particles which is hampering efforts to identify biomarkers that could help to better understand the mechanism of plaque formation, lead to early diagnosis and discovering efficient drugs to treat affected patients. Previously, an innovative Plaque Array method for in vitro detection and quantitation of serum derived plaque particles has been developed related to Atherosclerosis and AD (Madasamy, 2011, PCT/US2012/066412). In the present disclosure, a combination of flow cytometer and mass spectroscopy based approach is disclosed for an in vitro isolation, quantitation and biomarker identification from a wide range of plaque particles related to atherosclerosis, amyloidosis and other plaque related diseases.

As used herein, Abeta-42 refers to Amyloid beta peptide 1-42 and derivatives; Abeta-28 refers to Amyloid beta peptide 1-28 and derivatives; Abeta-17 refers to Amyloid beta peptide 1-17 and derivatives; Chl refers to cholesterol; LS refers to phospholipid; and CP refers to calcium phosphate.

The "plaque particles" and "in vitro plaque particles" disclosed herein refer to the same reaction product formed in the presence of added biological sample and the terms are used interchangeably. These terms are different from the term "self-formed plaque particles" which are formed in the absence of added biological sample. "Self-formed plaque particles" refers to one type of reagent used in the plaque array assay.

The plaque aggregates (including but not limited to) such as cholesterol plaque aggregate, phospholipid plaque aggregate, Abeta plaque aggregate, Tau plaque aggregate, alpha-synuclein aggregate, hybrid plaque aggregate and the like disclosed herein are water soluble. The self-formed plaque particle and the plaque particle disclosed herein however are water insoluble. The aggregates of various amyloid peptides disclosed herein as Abeta aggregates generally referred to in the literature as oligomers. As disclosed herein, an array or a panel refer to a plurality of plaque aggregates or self-formed plaque particles.

The plaque aggregates, plaque oligomers or self-formed plaque particles as disclosed to be used in screening biological samples or bio-fluids effect on plaque particle formation may comprise one or more of the following: Abeta peptides and derivatives:

TABLE 1

Shows the human sequences and their representative names.

| Sequence number | Name | Sequence |
|---|---|---|
| SEQ ID NO: 1 | Abeta 1-42 | DAEFRHDSGYEVHHQKLVFFAEDVGSNKGAIIGLMVGG-VVIA |
| SEQ ID NO: 2 | Abeta 1-28 | DAEFRHDSGYEVHHQKLVFFAEDVGSNK |
| SEQ ID NO: 3 | Abeta 1-17 | DAEFRHDSGYEVHHQKL |
| SEQ ID NO: 4 | Abeta 22-35 | EDVGSNKGAIIGLM |
| SEQ ID NO: 5 | Amyloid (1-42 S26C) | DAEFRHDSGYEVHHQKLVFFAEDVGCNKG-AIIGLMVGGVVIA |
| SEQ ID NO: 6 | Amyloid (1-42) | E22V-DAEFRHDSGYEVHHQKLVFFAVDVGSNKG-AIIGLMVGGVVIA |
| SEQ ID NO: 7 | Amyloid (1-42) | N27A-DAEFRHDSGYEVHHQKLVFFAEDVGSAKG-AIIGLMVGGVVIA |

Additionally sequences of Synuclein, prion, Amylin, Tau, phospholipids, cholesterol crystals, Serum Amyloid A, Beta Microglobulin, lysozyme, insulin, or super dioxide dismutase should also be considered.

In one embodiment, plaque aggregate, plaque oligomer or self-formed plaque particle comprise of at least one component known to be present in in vivo formed plaques in subjects with plaque related disease. In these embodiment, the component of may be linked to a detectable label. In other embodiments, plaque aggregates, plaque oligomer or self-formed plaque particles comprise of cholesterol or its derivatives. In another embodiment, plaque aggregates, plaque oligomer or self-formed plaque particles comprise phospholipid or its derivatives. In one embodiment, the plaque aggregates or the plaque oligomer comprise a single component while in other embodiment they are hybrid aggregates or oligomers and comprise more than one component.

In one embodiment, the plaque aggregates, plaque oligomer and self-formed plaque particles are prepared in phosphate buffered saline (PBS) or phosphate buffers. As an alternate any suitable aqueous solution may be used instead. In another embodiment, the plaque aggregates, plaque oligomer or self-formed plaque particles are prepared using organic solvents such as alcohol. In one embodiment, the reactions forming plaque aggregates and self-formed plaque particles are performed at 37° C. In other embodiment, the reaction is performed at a temperature and a time which are appropriate for progression of a reaction. In one embodiment the reactions using the plaque aggregates, plaque oligomer and self-formed plaque particles in diagnostic or drug discovery or development or other context are performed at 37° C. In other embodiment, the reaction is performed at a temperature and a time which are appropriate for progress of a reaction.

Any biological sample may be tested according to the disclosed methods. Such a sample may be cells, tissue, blood, urine, semen, or a fraction thereof (e.g., plasma, serum, urine supernatant, urine cell pellet or nerve or endothelial cells), which may be obtained from a patient or other source of biological material, e.g., autopsy sample or forensic material. Prior to contacting the plaque aggregates or plaque oligomer, the sample may be processed to isolate or enrich the sample for the desired molecules using a variety of standard laboratory practices which may be used for this purpose, such as, e.g., centrifugation, immunocapture, cell lysis. Bio-fluid is one category of biological sample. As disclosed herein, the term bio-fluid is a fluid biological sample and is used interchangeably with the term biological fluid. While the bio-fluid used in the examples disclosed herein is serum from human subjects, in one embodiment the bio-fluid may also comprise of plasma, saliva, urine, cerebrospinal fluid and/or blood.

Biological samples may be obtained from animals (including humans) and encompass fluids, solids, tissues, and gases. Biological samples may also include sputum, bronchial washing, bronchial aspirates, urine, lymph fluids, and various external secretions of the respiratory, intestinal and genitourinary tracts, tears, saliva, milk, biological fluids such as cell culture supernatants, tissue, cell, and the like.

The present application discloses an in vitro technology of detecting presence of a plaque particle, isolating the plaque particle followed by its composition analysis. Further, the present application also relate to understanding a mechanism of plaque formation, identifying a component of mechanism of plaque formation and a method of screening a candidate agent as an anti-plaque agent. More specifically, the present disclosure relates to an in vitro technology of isolating at least one plaque particle or plurality of plaque particles using a flow cytometer, separating the plaque particle based on different and selected physical parameters; analyzing the particle through mass spectroscopy and identifying biomolecules present in the plaque particle to predict a biomarker.

Further, the disclosure relates to a use of a plaque array method to screen candidate agents for the inhibition or stimulation of the in vitro formation of the plaque particles. As such, candidate agents including but not limited to chemical compounds, small molecule compounds, therapeutic drugs, biological molecules, oligomers, ligands, proteins, antibodies or other components, capable of binding the plaque aggregates or self-formed plaque particles or plaque particles in the presence or absence of bio-fluids, preventing their assembly, disassembling these aggregates or self-formed plaque particles or plaque particles once already formed, or reducing their pathogenic properties, are tested for their potential as therapeutic leads for diagnosing, preventing, treating, an d/or curing amyloid or atherosclerosis related plaque diseases. Since the methods or processes disclosed herein are capable of isolating the steps of in vitro plaque particle formation, anti-plaque agents targeting different stages of plaque development are also capable of being identified. The term "anti-plaque agents" and "anti-plaque therapeutics" are used interchangeably herein and refer to compounds or drugs which are effective in: a) dissolving, inhibiting or disrupting the architecture, or structure of a plaque aggregates or self-formed plaque particles or plaque particles described herein; and/or b) inhibiting, preventing, or alleviating the detrimental effects that the plaque may have on other cells, tissues or organs of humans.

In one embodiment, plaque particle(s) as formed following contacting are analyzed through plaque array technology. The plaque array technology permits the discovery of both novel mechanisms and molecules that catalyze the accelerated plaque particle assembly when treated with the biological samples. In one embodiment the plaque array enables the evaluation of the pathogenicity of plaques of varying compositions.

Thus, the present application discloses a methodology of isolating bio-molecule from a plaque particle with the following steps:
a. Preparation of plaque forming oligomer or aggregates;
b. Detection of plaque particles;
c. Sorting and isolation of plaque particles;
d. Processing of isolated particles for proteomics, glycomics, lipidomics and metabolomics analyses;
e. Spectroscopic analysis of peptides for identification of different proteins;
f. Spectroscopic analysis of lipids composition; and
g. Analyses of the glycans and metabolites composition.

Preparation of Plaque Forming Cholesterol, Phospholipid and Amyloid Oligomer/Aggregates:

The chemical structures of cholesterol, phospholipids, amyloid peptides and their derivatives used herein for preparation of plaque forming oligomers/aggregates has been described in previous applications (Madasamy, 2009, US Application No. 200901041211; Madasamy, 2011, PCT/US2012/066412; incorporated herein by reference). Briefly, 1 mg of lyophilized fluorescently-labeled cholesterol or cholesterol derivatives (Ex/Em=495 nm/507 nm) was solubilized in 1 mL of 100% alcohol. From this stock solution, 100 µL was taken and mixed in 900 µL of PBS. The samples were centrifuged for 5 min. at 5000 rpm to remove precipitates, if any, and the supernatant containing mostly soluble oligomer/aggregates were used for in vitro plaque particles formation assay.

To prepare phospholipids plaque aggregates, 1 mg of fluorescently-labeled-phospholipids or its derivatives (Ex/Em=495 nm/507 nm) was solubilized in 1 mL of 100% alcohol. From this stock solution, 100 µL was taken and mixed in 900 µL of PBS. The samples were centrifuged for 5 min. at 5000 rpm to remove precipitate, if any, and the supernatant containing plaque aggregates were used for plaque array assay. The transfer of esterified cholesterol and phospholipid molecules from organic medium (alcohol) to PBS buffer lead to transformation of soluble molecules into oligomers/aggregates.

To prepare Abeta-42 oligomers/aggregates, 1 mg of fluorescently-labeled Abeta-42 peptide was suspended in 1 mL of PBS and the sample was incubated at 37° C. for 2 hrs. The samples were centrifuged for 5 min. at 5000 rpm to remove precipitate, if any, and the supernatant containing oligomers/aggregates were used for plaque array assay. Similarly, to prepare unlabeled Abeta-42 aggregates, 1 mg of Abeta-42 peptide was suspended in 1 mL of PBS and the sample was incubated at 37° C. for 2 hrs. For Abeta-28 aggregates preparation, 1 mg of Abeta-28 was suspended in 1 mL of PBS and the sample was incubated at 37° C. for 2 hrs. The samples were centrifuged for 5 min. at 5000 rpm to remove precipitate, if any, and the supernatant containing oligomers/aggregates were used for in vitro plaque particles formation assay. For detecting unlabeled amyloid plaque particles Thioflavin S (Ex/Em=430 nm/550 nm) amyloid binding fluorescent dye (10 µg) was used.

To prepare derivatives of human Tau proteins oligomers/aggregates, 1 mg of Tau-45 Peptide (45-73 Exon 2/Insert 1 domain) was suspended in 1 mL of PBS and the sample was incubated at 37° C. for 2 hrs. For Tau-74 (74-102) (Exon 3/Insert 2 domain) preparation, 1 mg of Tau-74 was suspended in 1 mL of PBS and the sample was incubated at 37° C. for 2 hrs. Similarly for preparing Tau-275 (275-305) (Repeat 2 domain) 1 mg of the peptide was suspended in 1 mL of PBS and the sample was incubated at 37° C. for 2 hrs. After incubation, all the samples were centrifuged for 5 min. at 5000 rpm to remove precipitate, if any, and the supernatant containing oligomers/aggregates were used for in vitro amyloid plaque particles formation assay. For detecting Tau plaque particles, Thioflavin S (Ex/Em=430 nm/550 nm) amyloid binding fluorescent dye (10 µg) was used in the assay.

To prepare oligomers/aggregates of human alpha-synuclein (140 amino acids polypeptide), 1 mg of the recombinant alpha-synuclein protein was suspended in 1 mL of PBS and the sample was incubated at 37° C. for 2 hrs. After incubation, all the samples were centrifuged for 5 min. at 5000 rpm to remove precipitate, if any, and the supernatant containing oligomers/aggregates were used in vitro plaque particles formation assay. For detecting alpha-synuclein plaque particles Thioflavin S (Ex/Em=430 nm/550 nm) amyloid binding fluorescent dye (10 µg) was used.

Flow Cytometer Based Detection of Cholesterol, Phospholipd Amyloid Plaque Particles:

Human serum and plasma samples obtained from patients previously diagnosed for atherosclerosis related cardiovascular diseases and AD were used for examining in vitro cholesterol, phospholipid and amyloid plaque particles formation respectively. The plasma or serum samples were first centrifuged at 5,000 rpm for 5 min and the supernatants were transferred to new centrifuge tubes. Next, the supernatants were diluted in PBS to make 50% of the serum and/or plasma. The diluted samples were used for incubation with plaque forming oligomers/aggregates or self-formed plaque particles to examine in vitro plaque particle synthesis. Each assay was performed in a 200 µL reaction (100 µL of 50% plasma or serum) and 100 µL (5 µg) of the Cholesterol oligomers/aggregates and the mixtures were incubated at 37° C. for 1 hr. After the incubation, 100 µL sheath fluid was added to the mixture and the samples were used for acquisition (1-2000 events/particles for 1 min) in flow cytometer.

For detecting cholesterol plaque particles formation in the serum or plasma samples, fluorescently labeled cholesterol oligomers/aggregates prepared were used for incubation with serum samples. Each in vitro plaque particle formation assay was performed in a 200 µL reaction (100 µL of 50% plasma or serum and 100 µL (5 µg) of the fluorescently-labeled cholesterol self-formed plaque particles and the mixtures were incubated at 37° C. for 1 hr After the incubation, 100 µL sheath fluid was added to the mixture and the resulting samples were analyzed in the flow cytometer.

Next, fluorescently-labeled phospholipid plaque aggregates were prepared and used for screening the serum and plasma samples. For control experiment, fluorescently-labeled plaque aggregates were incubated in PBS and not treated with the serum. Each in vitro plaque particle formation assay was performed in a 200 μL reaction (100 μL of 50% plasma or serum and 100 μL (5 μg) of the phospholipid plaque aggregates and the mixtures were incubated at 37° C. for 1 hr. After the incubation, 100 μL sheath fluid was added to the mixture and the resulting samples were analyzed by flow cytometry.

The following assays were performed with the Abeta oligomers/aggregates. Each assay was performed in a 200 μL reaction (100 μL of diluted serum with final concentration of 25% and 100 μL (5 μg) of the unlabeled Abeta-42 or Abeta-28 aggregates and the mixtures were incubated at 37° C. for 1 hr for in vitro plaque particle formation. After incubation with diluted serum, 10 μL of Thioflavin S (Ex/Em=430 nm/550 nm) fluorescent dye (10 μg) was added and the sample was incubated for an additional 30 min. at 37° C. Following incubation, 100 μL sheath fluid was added to the mixture and the samples were used for acquisition (2000 events/particles per min) in flow cytometer.

Flow Cytometer Based Sorting and Isolation of Cholesterol and Amyloid Plaque Particles:

The goal was to isolate plaque particles synthesized in the bio-fluids in a relatively pure form to enable their subsequent use for identification of components that contribute to the plaque formation. In order to isolate cholesterol plaque particles, the plasma or serum samples obtained from atherosclerotic subjects were first centrifuged at 5,000 rpm for 5 min and the supernatants were transferred to new centrifuge tubes. Next, the supernatants were diluted in PBS to make 50% of the serum and used for incubation with cholesterol oligomers/aggregates. Each assay was performed in 1 mL reaction (800 μL of 50% plasma or serum) and 200 μL (30 μg) of the Cholesterol aggregates and the mixtures were incubated at 37° C. for 1 hr After the incubation, the mixture was directly used for sample acquisition using flow cytometer (FACS ARIA II, BD Biosciences, San Jose, Calif.). The acquisition and fluorescent dot blot analysis showed two major fractions of fluorescent cholesterol plaque particles. In order to isolate these fractions, three sets of gates were drawn in the acquisition blot to separately sort and isolate High density or high complex cholesterol particles, Low density or low complex cholesterol particles and both High and low density cholesterol particles together. The total number of cholesterol particles sorted and collected in separate tubes varied (5000 to 100,000) among serum samples of atherosclerosis subjects.

Next to isolate serum derived Abeta-42 plaque particles, the plasma or serum samples obtained from AD subjects were first centrifuged at 5,000 rpm for 5 min and the supernatants were transferred to new centrifuge tubes. Next, the supernatants were diluted in PBS to make 50% of the serum and plasma samples and used for incubation with Abeta-42 plaque oligomers/aggregates. Each assay was performed in 1 mL reaction (800 μL of 50% plasma or serum) and 200 μL (30 μg) of the Abeta-42 aggregates and the mixtures were incubated at 37° C. for 1 hr. To the mixture Thioflavin S dye (120 μg) was added and the sample was incubated for additional 30 min at 37° C. After the incubation, the mixture was directly used for sample acquisition using flow cytometer (FACS ARIA II, BD Biosciences, San Jose, Calif.). After initial detection of Abeta-42 plaque particles in the acquisition blot, gates were drawn in fluorescent dot blot to separately sort and isolate fluorescently labeled Abeta-42 particles. The total number of particles sorted and collected in separate tubes varied from 5000 to 100,000.

Similarly, to isolate serum derived Abeta-28 plaque particles, the plasma or serum samples obtained from AD subjects were first centrifuged at 5,000 rpm for 5 min and the supernatants were transferred to new centrifuge tubes. Next, the supernatants were diluted in PBS to make 50% of the serum and plasma samples and used for incubation with Abeta-28 plaque oligomers/aggregates. Each assay was performed in 1 mL reaction (800 μL of 50% plasma or serum) and 200 μL (30 μg) of the Abeta-28 aggregates and the mixtures were incubated at 37° C. for 1 hr. To the mixture Thioflavin S dye (120 μg) was added and the sample was incubated for additional 30 min at 37° C. After the incubation, the mixture was directly used for sample acquisition using flow cytometer (FACS ARIA II, BD Biosciences, San Jose, Calif.). After initial detection of Abeta-28 plaque particles, gates were drawn to separately sort and isolate fluorescently labeled Abeta-28 particles.

Next, to isolate Tau plaque particles, as performed for Abeta-42 and Abeta-28 plaque particles isolation, diluted serum samples were used for incubation separately with Tau-45, Tau-74 and Tau-275 oligomers/aggregates. Each assay was performed in 1 mL reaction (800 μL of 50% plasma or serum) and 200 μL (30 μg) of each Tau aggregates and the mixtures were incubated at 37° C. for 1 hr. To the each mixture Thioflavin S dye (120 μg) was added and the sample was incubated for additional 30 min at 37° C. After the incubation, each sample was directly used for sample acquisition using flow cytometer (FACS ARIA II, BD Biosciences, San Jose, Calif.). After initial detection of Tau plaque particles, gates were drawn in the acquisition blot to separately sort and isolate fluorescently labeled Tau plaque particles.

Similarly, to isolate alpha-synuclein plaque particles, diluted plasma or serum samples obtained from AD subjects were used for incubation with alpha-synuclein plaque oligomers/aggregates. Each assay was performed in 1 mL reaction (800 μL of 50% plasma or serum) and 200 μL (30 μg) of the alpha-synuclein aggregates and the mixtures were incubated at 37° C. for 1 hr. To the mixture Thioflavin S dye (120 μg) was added and the sample was incubated for additional 30 min at 37° C. After the incubation, the mixture was directly used for sample acquisition using flow cytometer (FACS ARIA II, BD Biosciences, San Jose, Calif.). After initial detection of alpha-synuclein plaque particles, gates were drawn in the acquisition blot to separately sort and isolate fluorescently labeled alpha-synuclein particles.

Processing of Isolated Plaque Particles for Mass Spectrescopy Based Proteomics and Glycomics Analyses:

For preparing trypsin digested peptide sequences, the isolated plaque particles were centrifuged at 10000 rpm for 5 min and the pellet containing plaque particles was resuspended in 100 μl PBS buffer. Stock solutions of digestion buffer (Ammonium Biocarbonate 50 mM), reducing buffer (DDT 100 mM) and alkylation buffer (Iodoaceamide 100 mM) were prepared and stored at −20° C. for up to two months. For trypsin digestion, 100 μl of each plaque particles (2000 of Abeta-42, cholesterol, Tau and alpha-synuclein) were precipitated using cold acetone −80° C. by adding 4X's the volume. The samples were placed on dry ice for 10 min with intermittent vortex. Next, the samples were centrifuged at 4° C. at 10000 G for 10 min. Top layer of acetone was carefully removed from the tube with care not to disturb the plaque particles pellet. The samples were speed-vac for 10 min to ensure all acetone has been boiled away. The plaque particles pellet were reconstituted with 15 μl 8M Urea 100 mM Ammonium bicarbonate stock and 20 μl protease max solution. The protease max solution (Promega, Madison, Wis.) was prepared from stock by adding 60 μl 50 mM Ammonium bicarbonate and used for 3 solution digests (20 μl each). Once protease is added, the samples were vortexed on low level sonication for 10-30 minutes for ensured protein solubility followed by addition of 1.6 μl of the 500 mM DTT stock to each tube. The tubes were incubated at 55° C. for 30 minutes. The tubes were then removed and brought to the room temperature followed by addition of 3.2 μl of 1M acrylamide and incubated at room temperature for 30 minutes. To the sample, 63 μL of 50 mM Ammonium bicarbonate was added for a final volume of 98 μl and 2 μl of trypsin (10 μg, Trypsin/Lys C Mix). After mixing the solution with pipet the samples were incubated at 37° C. overnight. After the overnight digest, the tryptic digest were quenched and acidified by adding 10 μl of 50% formic acid/water stock dilution. The samples were centrifuged at 10000 G for 2 minutes and purified using stage tip and used for MS/Mass analysis.

For glycomics study, one part of the tryptic digests is used for enrichment using lectin column and the eluted glycopeptides are digested with PNGase F enzyme. at 37° C. for overnight. α-Mannosidase digestion is carried out on PNGase F-released glycans using the alpha-mannosidase enzyme, The enzyme digestion was incubated at 37° C. for 48 h with a fresh aliquot of enzyme added after 24 h and terminated by boiling for 10 min. After drying in a vacuum centrifuge the samples e re-dissolved in 10 μL 0.1% TFA and subjected Mass spec analyses using the same conditions used for the identification of plaque particles proteins Mass Spectroscopy Analysis of Peptides for Identification of Proteins:

All MS/MS samples were analyzed using Sequest (Thermo Fisher Scientific, San Jose, Calif., USA; version 1.0). Sequest was set up to search the SUMS_uniprot_Human database (35847 entries) assuming the digestion enzyme strict trypsin. Sequest was searched with a fragment ion mass tolerance of 1.00 Da and a parent ion tolerance of 20 PPM. Propionamide of cysteine was specified in Sequest as a fixed modification. Oxidation of methionine and phospho of serine, threonine and tyrosine were specified in Sequest as variable modifications.

Scaffold (version Scaffold_4.2.1, Proteome Software Inc., Portland, Oreg.) was used to validate MS/MS based peptide and protein identifications. Peptide identifications were accepted if they could be established at greater than 95.0% probability by the Peptide Prophet algorithm (Keller, A et al, 2002) with Scaffold delta-mass correction. Protein identifications were accepted if they could be established at greater than 99.0% probability and contained at least 1 identified peptide. Protein probabilities were assigned by the Protein Prophet algorithm (Nesvizhskii, Al et al 2003). Proteins that contained similar peptides and could not be differentiated based on MS/MS analysis alone were grouped to satisfy the principles of parsimony. Proteins sharing significant peptide evidence were grouped into clusters. Proteins were annotated with GO terms from NCBI (downloaded Jan. 17, 2014).

Plaque Particles Processing for Mass Spec Based Lipidomics Analysis:

Cholesterol and amyloid plaque particles sorted (5,000 particles each) were used for lipid extraction. 30 uL of each plaque particles was mixed with 200 uL MeOH to which 300 uL chloroform was added. The samples were vortexed thoroughly and incubated at room temperature for 10 minutes. Then, 120 uL H2O was added to the sample and vortexed briefly. The samples were centrifuged at 10,000 rpm for 10 min to separate phases. After centrifugation 40 uL of the lower layer was transferred to an eppendorf tube and diluted with 160 uL injection solvent (65:30:5 acetonitrile/isopropanol/water) for LC-MS analysis. The samples were used for lipidomics analysis by LC/MS on an Agilent 1260 HPLC and Bruker microTOF-Q II mass spectrometer. Full scan ms data was acquired in positive ion mode. The column was a Waters Atlantis T3 3u 2.1×100 mm with initial conditions of 60% A (60:40 acetonitrile/water with 10 mM ammonium formate)/40% B (90:10 acetonitrile/isopropanol). The flow rate was 0.4 mL/minute.

Also provided by the subject application are kits for use in practicing one or more of the above described applications embodiment. The present invention discloses a plaque array kit to aid in the diagnosis, prediction, prognosis, or detection of a plaque-associated disease such as AD and atherosclerosis. In one embodiment, the kit comprises one or more molecules for preparing plaque aggregates, or plaque oligomer as described herein along with reagents of plaque array assay and detection of plaque particles by flow cytometer or luminescence detector.

In one embodiment, the present application also discloses kits for detection of biomarkers for early diagnosis of subject sample for plaque-associate disease. The kit may include: one or more molecules for preparing plaque aggregates or plaque oligomers; materials to collect and store biological sample from a patient; reagents for incubating biological sample with the plaque aggregate or the plaque oligomer; isolating the plaque particle; detecting the presence of plaque particle; and analyzing the plaque particle through flow cytometer. Further, the kit as disclosed may also contain materials for preparing plaque particle sample for mass spectroscopy for further composition analysis.

In one embodiment instructions teaching the use of the kit according to the various methods and approaches described herein are provided. Such kits may also include information, such as scientific literature references, package insert materials, clinical trial results, and/or summaries of these and the like, which indicate or establish the activities and/or advantages of the agent. Kits described herein can be provided, marketed and/or promoted to health providers, including physicians, nurses, pharmacists, formulary officials, and the like.

EXAMPLES

The following additional examples are offered by way of illustrations and not by way of limitation.

Example 1

Overview of the Flow Cytometer and Mass Spectroscopy Based Biomarkers Identification Method from Plaque Particles The Example illustrated in FIG. 1 includes both a schematic diagram and steps involved in the denvelopment of plaque array method in combination with Mass spectroscopy. This method involves steps for detection, quantitation, isolation, proteomics, glycomics, lipidomics and metabolomics analysis of plaque particles.

FIG. 1 represents a schematic of the Flow cytometer and Mass spectroscopy based detection, sorting and biomarkers identification in plaque particles. Step 1, in vitro formation of insoluble plaque particles in bio-fluids; step 2, Flow cytomer based identification and isolation of plaque particles; step 3A, trypsin digestion of the isolated plaque particles to prepare peptide fragments: step 3B, extraction of lipid or metabolites from plaque particles; step 4A, Mass spectroscopy (MS/MS) based proteomics and glycomics for identification of proteins/glycoproteins and step 4B, GC/MS based identification of lipids or metabolites.

Example 2

Flow Cytometer Based Detection and Quantitation of Abeta-42 Plaque Particles in AD Serum Sample Amyloidosis is a group of more than fifteen neurodegenerative or protein aggregation diseases caused mainly by deposition of misfolded amyloid proteins or their derivatives in both intra cellular and extracellular regions of brain. The amyloid plaque related protein aggregation diseases include AD, PD, prion-mediated diseases, Tau pathies, HD, MS, type 2 diabetes and the like. Among them AD is the most common and serious neurodegenerative disease associated with progressive dementia caused mostly due to the deposition of Amyloid-beta (Abeta) peptides (Yankner 1996). Abnormal processing of the Abeta precursor protein is an early and causative event in the pathogenesis of AD (Selkoe D. J. 2003). Amyloid precursor protein (APP) undergoes a series of proteolytic cleavages culminating in production of Abeta-42 peptides and smaller peptides.

Figure 2A:
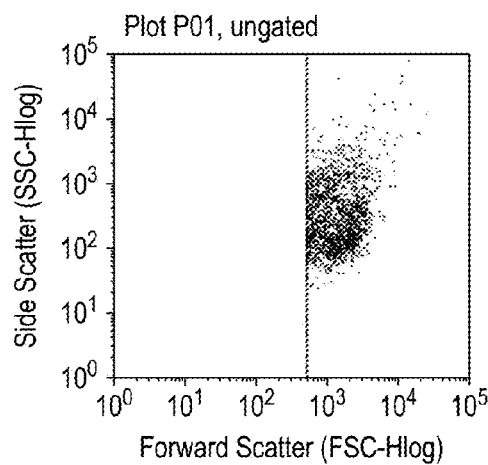
FIGS. 2A, 2B and 2C represents a flow cytometer based detection of Abeta-42 plaque particles.
Figure 2B:
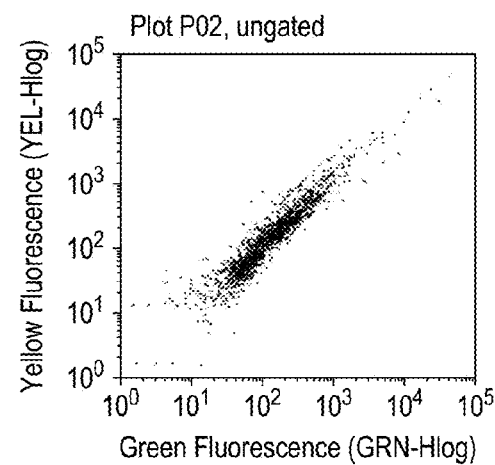
Figure 2C:
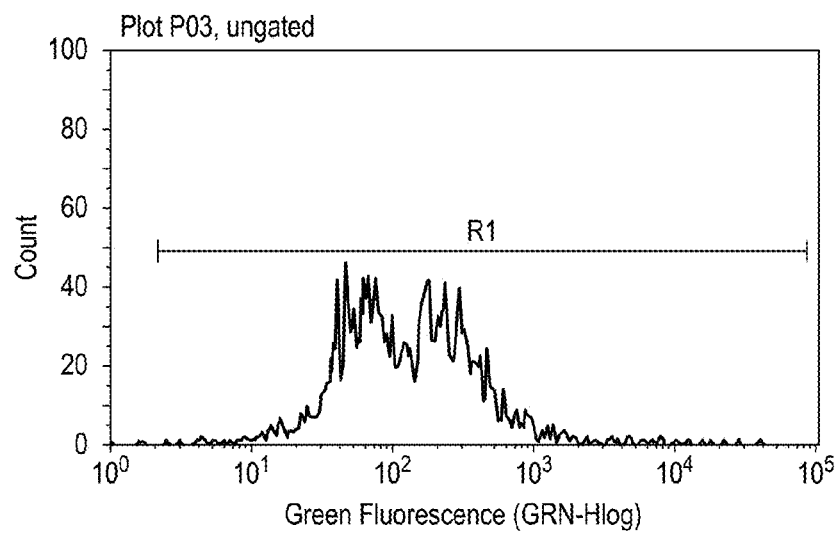

In order to examine abeta peptides based amyloid plaque particles formation in the bio-fluids, experiments were carried out using Abeta-42 oligomers/aggregates incubated in the diluted serum samples. After incubation the samples were used for analysis in Flow cytometer. The results of flow cytometry displayed herein are typically presented as one dimensional histogram on a logarithmic scale or two-dimensional displays (dot plot) with logarithmic axes that can extend over a four- to five-decade range. FIG. 2A shows detection of Abeta-42 plaque particles in acquisition dot blot. FIG. 2B shows detection of fluorescence (Thioflavin S) positive Abeta-42 plaque particles and FIG. 2C shows counting of fluorescence plaque particles. In the assay, the Abeta-42 oligomers/aggregates acts as "substrate" and serum components act as "catalyzers" converting the soluble aggregates into insoluble plaque particles that are efficiently detected in the Flow cytometer. The concentrations of serum derived abeta-42 based plaque particles load in AD subjects are in the range of ~6000 to 64,000/mL whereas in the normal subjects the concentrations are ~300 to 5000/mL. The results also indicate that both specific and non-specific binding of serum ligands to the soluble plaque aggregates/oligomers lead to formation of insoluble plaque particles that are detected by flow cytometer.

FIGS. 2A, 2B and 2C shows a flow cytometer based detection of Abeta-42 plaque particles. 2A shows an acquisition dot blot analysis of plaque particles in both side scattering (y-axis) and forward scattering (x-axis); 2B shows fluorescence dot blot analysis of plaque particles (x-axis 520 nm; y-axis 560 nm). The two-dimensional displays (dot plot) with logarithmic axes that can extend over a four- to five-decade range. In these plots, starting at x=0, y=0, the tick marks on the x-axes and y-axes represent fluorescent intensity of $10^0$, $10^1$, $10^2$, $10^3$ and $10^4$ respectively and 2C shows histogram blot showing plaque particles count (Fluorescence 520 nm).

Example 3

Flow Cytometer Based Detection and Quantitation of Abeta-28 Plaque Particles in AD Serum Sample To examine plaque particles formation in the AD patient serum sample, a different derivative of abeta peptide, Abeta-28, was used. Diluted serum sample was incubated with Abeta-28 oligomer/aggregates and after staining with Thioflavin S dye the samples were analyzed in Flow cytometer. As observed with Abeta-42 plaque particles formation described in example 2, the soluble form of aggregates are readily converted in to insoluble Abeta-28 plaque particles that are detected by the Flow cytometer. FIG. 3A shows Abeta-28 plaque particles detection in acquisition dot blot, fluorescence dot blot and histogram analysis. These results indicate that serum samples of AD patients contain molecules that can accelerate the synthesis of insoluble plaque particles from the undetectable plaque oligomers/aggregates.

FIGS. 3A, 3B and 3C shows a flow cytometer based detection of Abeta-28 plaque particles. 3A shows acquisition dot blot displays plaque particles in both side scattering (y-axis) and forward scattering (x-axis); 3B shows fluorescence dot blot displays plaque particles (x-axis 520 nm; y-axis 560 nm). The two-dimensional displays (dot plot) with logarithmic axes that can extend over a four- to five-decade range. In these plots, starting at x=0, y=0, the tick marks on the x-axes and y-axes represent fluorescent intensity of $10^0$, $10^1$, $10^2$, $10^3$ and $10^4$ respectively and 3C shows histogram blot displaying plaque particles count (Fluorescence 520 nm).

Example 4

Flow Cytometer Based Detection of Cholesterol Particles in Atherosclerosis Patient's Serum Samples Atherosclerosis is a chronic inflammatory cardiovascular disease caused by development of atherosclerotic plaque in the arteries. Both dyslipidemia and hypercholesterolemia are linked to initiation and progression of atherosclerosis related cardiovascular complications (Grundy S M et al, 2014; Yuasa et al, 2014). More specifically, elevated serum levels of low density cholesterol particles and reduced levels of high density cholesterol particles are known risk factors for atherosclerosis related fatal symptomatic events such as myocardial infarction and stroke (Kones R, 2011).

The following experiments were carried out to probe cholesterol particles formation in the serum samples of patients previously diagnosed with atherosclerosis. Fluorescently labeled cholesterol aggregates were incubated with diluted serum samples and the resulting sample was used for Flow cytometer analysis. FIG. 4 shows detection of cholesterol plaque particles acquired using dot blot, fluorescence dot blot and histogram blots. Two major fractions of cholesterol particles were observed in all blots. The lower density cholesterol particles (LD-Chl) or low complex cholesterol particles concentration was higher compared to higher density cholesterol particles (HD-Chl) or high complex cholesterol particles. It was observed that ~35% of the AD serum samples showed higher number of total cholesterol particles load (~10000 to 70000/mL). As observed with abeta plaque particles formation in serum samples, cholesterol oligomer/aggregates were converted into insoluble plaque particles by serum components present in atherosclerosis patients.

Figure 4A:
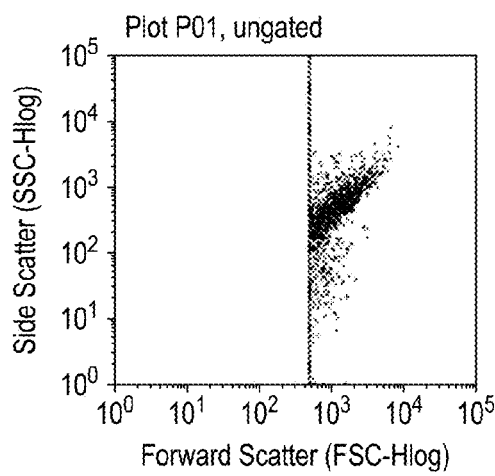
FIGS. 4A, 4B and 4C represents a flow cytometer based detection of cholesterol plaque particles.
Figure 4B:
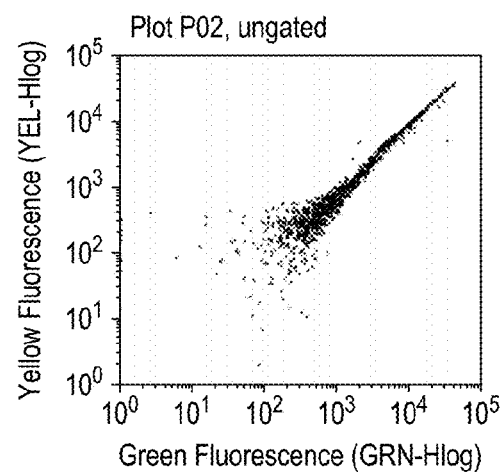
Figure 4C:
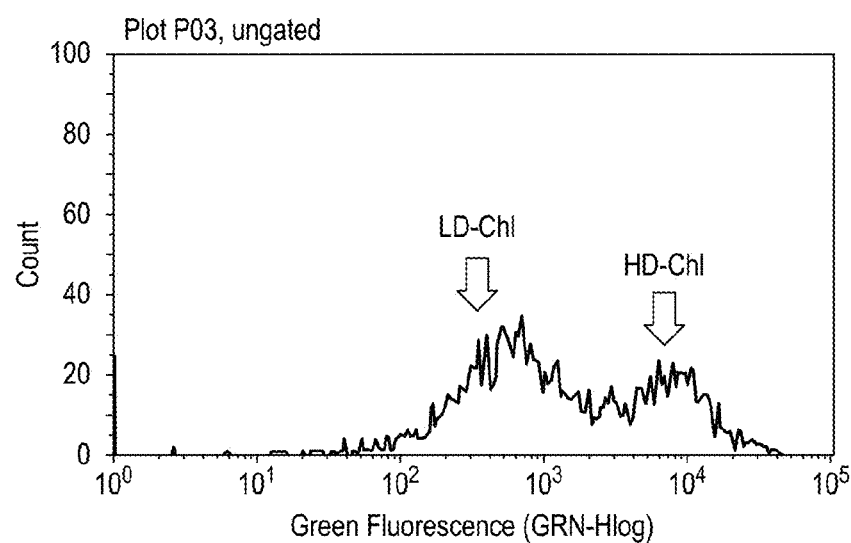

FIGS. 4A, 4B and 4C show a flow cytometer based detection of cholesterol plaque particles. 4A shows acquisition dot blot displays plaque particles in both side scattering (y-axis) and forward scattering (x-axis); 4B shows fluorescence dot blot displays plaque particles (x-axis 520 nm; y-axis 560 nm). The two-dimensional displays (dot plot)

with logarithmic axes that can extend over a four- to five-decade range. In these plots, starting at x=0, y=0, the tick marks on the x-axes and y-axes represent fluorescent intensity of $10^0$, $10^1$, $10^2$, $10^3$ and $10^4$ respectively and, 4C shows histogram blot (Fluorescence 520 nm). LD-Chl refers to low density or low complex cholesterol plaque particles; HD-Chl refers to high density or high complex cholesterol plaque particles.

Example 5

Flow Cytometer Based Detection of Phospholipids Particles in Atherosclerosis Patient's Serum Samples To further understand atherosclerotic plaque particles formation in the serum samples, phospholipid aggregates were prepared and incubated in the serum samples obtained from atherosclerosis patients. Flow cytometer analysis of the resulting samples showed two major fractions of phospholipid particles, similar to the results observed for cholesterol particles (FIG. 5).

Figure 5A:
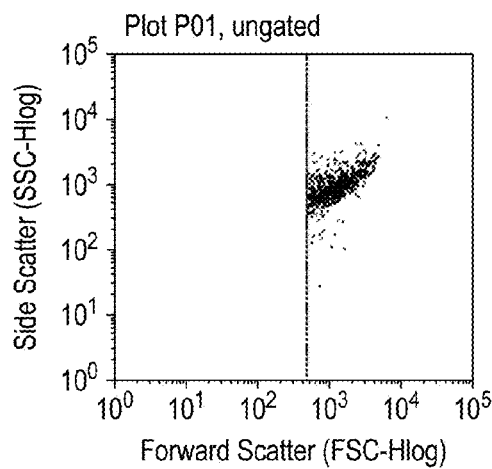
FIGS. 5A, 5B and 5C represents a flow cytometer based detection of phospholipids plaque particles.
Figure 5B:
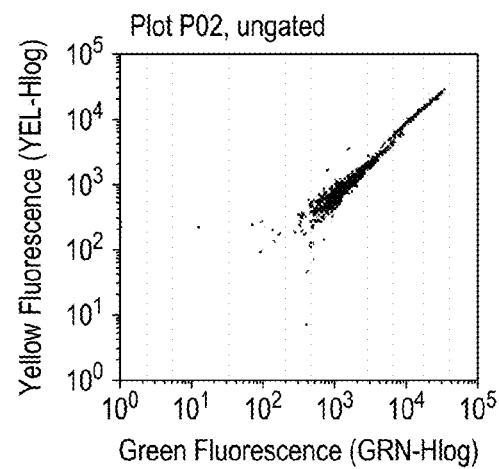
Figure 5C:
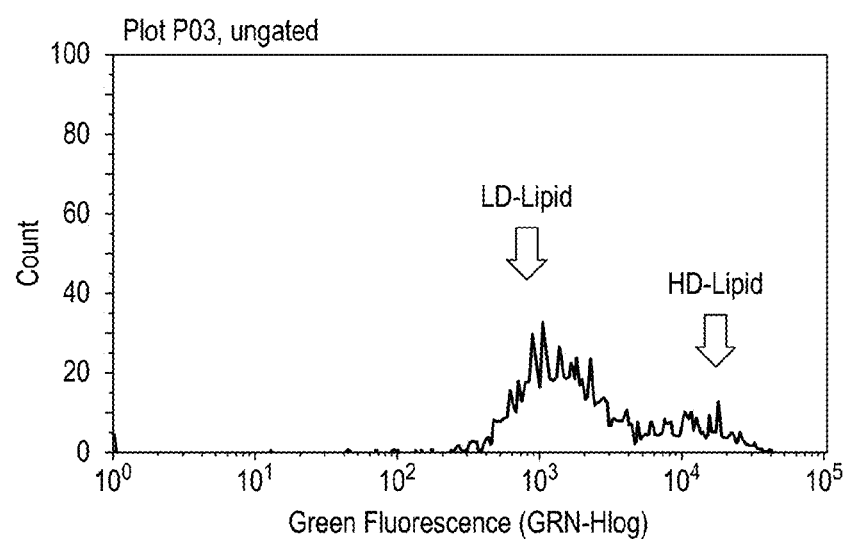

FIGS. 5A, 5B and 5C shows detection of phospholipids plaque particles using flow cytometer. 5A shows acquisition dot blot displays plaque particles in both side scattering (y-axis) and forward scattering (x-axis); 5B shows fluorescence dot blot analysis of plaque particles (x-axis 520 nm; y-axis 560 nm). The two-dimensional displays (dot plot) with logarithmic axes that can extend over a four- to five-decade range. In these plots, starting at x=0, y=0, the tick marks on the x-axes and y-axes represent fluorescent intensity of $10^0$, $10^1$, $10^2$, $10^3$ and $10^4$ respectively and 5C shows histogram blot analysis of (Fluorescence 520 nm) LD-Lipid refers to low density or low complex lipid plaque particles; HD-Lipid refers to high density or high complex plaque particles.

Taken together, the results of the Abeta-42, Abeta-28, cholesterol and phospholipids as plaque particles formation in the serum samples strongly indicate that the molecules present in the bio-fluids act as catalyzers to accelerate in vitro plaque particles formation. The serum samples of AD and atherosclerosis subjects contain components that catalyze in vitro formation of plaque particles from plaque forming soluble oligomers/aggregates. These results confirm our previous observation of accelerated plaque particles formation in AD and atherosclerosis serum samples compared to normal subjects (Madasamy, 2011, PCT/US2012/066412). The human serum or plasma is a complex biological fluid known to contain approximately 10,500 proteins, $10^7$ variants of antibodies and thousands of other metabolites. However, among these large pools of molecules the specific group of molecules involved in the plaque formation is not completely identified. Accordingly, it is important to identify molecules in the bio-fluids that might play either direct or indirect role in the plaque particles formation. It is possible that the plaque forming oligomers/aggregates used herein may be entangled in a specific and non specific binding with a wide range of ligands including proteins, antibodies, lipids, carbohydrates, metals and metabolites. Identification of such biomarkers could significantly help to better understand the complex mechanism of in vivo plaque development, aid in the development of biomarkers based diagnosis, patient stratification and discovery of mechanism based anti-plaque drugs.

Example 6

Figure 6C:
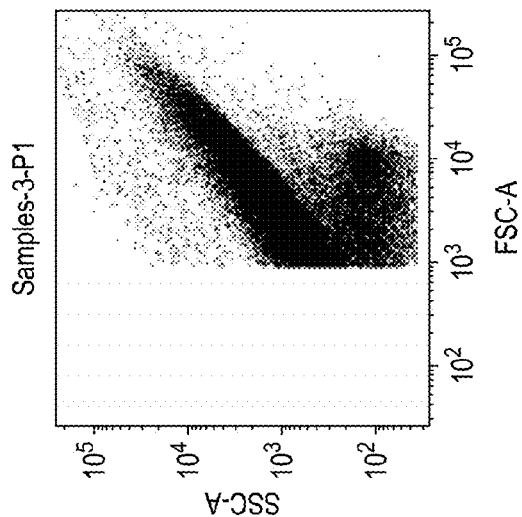
FIGS. 6A, 6B and 6C represents a flow cytometer based sorting and isolation of cholesterol plaque particles.
Figure 6B:
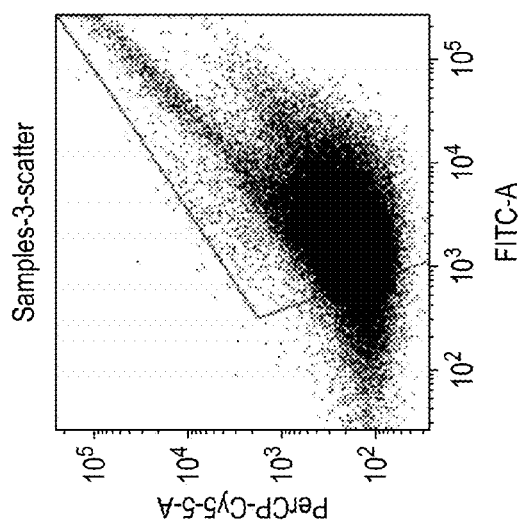
Figure 6A:
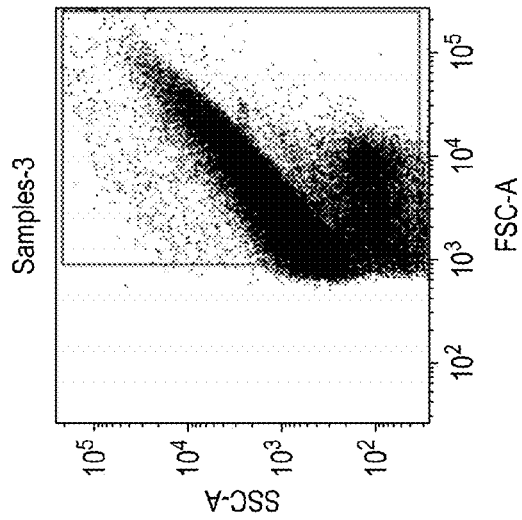

Flow Cytometer Based Sorting and Isolation of Serum Derived Cholesterol Plaque Particles Development of a rapid, sensitive and effective method for isolation of plaque particles is perquisite for biomarkers identification in the plaque particles. The preceding results described in the examples 2, 3, 4 and 5 show successful use of flow cytometer for detection, quantitation and identification of sub types of the plaque particles. In the next step, effort was made to isolate different types of plaque particles using flow cytometer based sorting method. Flow cytometer is widely used instrument to characterize, sort and isolate specific cell types (Piyasena Me. et al, 2014). Herein we describe isolation of fluorescence positive plaque particles using flow cytometer based sorting approach. First, fluorescence labeled cholesterol oligomer/aggregates were incubated in AD serum samples and used for sorting. FIG. 6A displays detection of two major fractions of cholesterol particles, FIG. 6B shows gating regions selected to sort large size cholesterol particles (5 to 60 microns in sizes) and FIG. 6C show isolated cholesterol particles. The isolated cholesterol particles (100,000) were stored at 4° C. and used for Mass spec analysis.

FIGS. 6A, 6B and 6C shows a flow cytometer based sorting and isolation of Cholesterol plaque particles. 6A shows acquisition blot displays detection of plaque particles in both side scattering (y-axis) and forward scattering (x-axis); 6B shows gating of fluorescence positive plaque particles population for sorting (x-axis 520 nm; y-axis 560 nm) and 6C shows acquisition blot displays sorting and isolation of gated fluorescence cholesterol plaque particles population. FSC refers to Forward scattering and SSC refers to side scattering.

Example 7

Sorting and Isolation of Serum Derived High Density and Low Density Cholesterol Plaque Particles The results observed in example 4, suggest although the cholesterol oligomer/aggregates were prepared from a homogenous form of cholesterol when the aggregates are incubated in the serum it is converted into two major fractions of cholesterol particles. It was of interest to examine the composition of both types of cholesterol particles (high density or high complex cholesterol particles and low density or low complex cholesterol particles) separately.

FIG. 7A displays two types of cholesterol particles in acquisition blot, FIG. 7B shows double gating of cholesterol particles for sorting and isolation and FIG. 7C shows high density and low density cholesterol particles isolated separately. These cholesterol plaque particles (100,000) were stored at 4° C. until use for Mass Spec analysis.

Thus, FIGS. 7A, 7B and 7C shows a flow cytometer based sorting and isolation of High density and low density cholesterol plaque particles. 7A shows acquisition dot blot showing detection of plaque particles in both side scattering (y-axis) and forward scattering (x-axis); 7B shows gating of fluorescence plaque particles population selected for sorting (x-axis 520 nm; y-axis 560 nm) and 7C shows sorting and isolation of gated fluorescence population of high density and low density plaque particles (x-axis 520 nm; y-axis 560 nm).

Example 8

Flow Cytometer Based Sorting and Isolation of Abeta-42 Plaque Particles

Figure 8C:
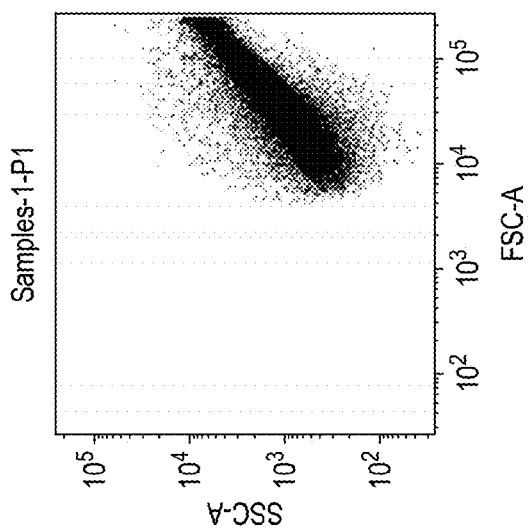
FIGS. 8A, 8B and 8C represents a flow cytometer based sorting and isolation of Abeta-42 plaque particles.
Figure 8B:
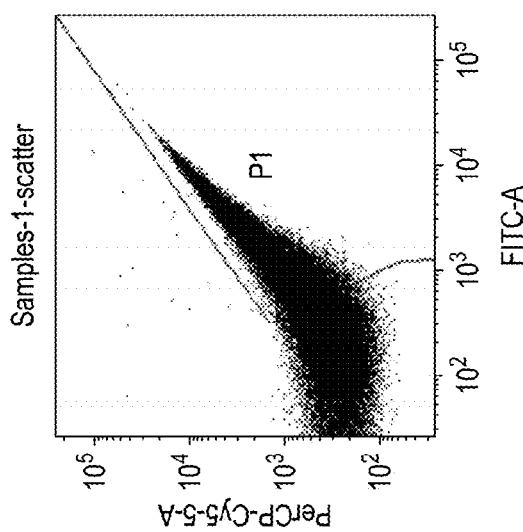
Figure 8A:
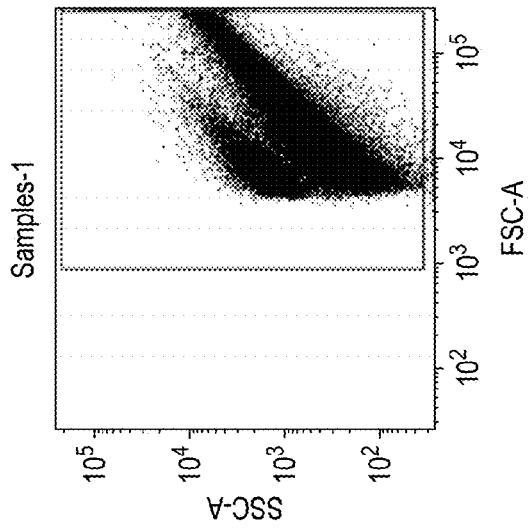

In the next step, flow sorting experiments were repeated for isolation of Abeta-42 particles. Abeta-42 aggregates incubated in the AD serum samples were stained with Thioflavin S dye and the resulting sample was used for sorting to collect 100,000 particles. FIG. 8A shows detection of Abeta-42 particles in acquisition dot blot and FIG. 8B shows gating of large Thioflavin S positive abeta particles selected for sorting. FIG. 8C show isolated Abeta-42 plaque particles.

Thus, FIG. 8 shows a flow cytometer based sorting and isolation of Abeta-42 plaque particles. 8A shows acquisition blot displays detection of plaque particles in both side scattering (y-axis) and forward scattering (x-axis); 8B show gating of fluorescence positive plaque particles population for sorting (x-axis 520 nm; y-axis 560 nm) and 8C shows acquisition blot displays sorting and isolation of gated fluorescence Abeta-42 plaque particles population. FSC refers to Forward scattering and SSC refers to side scattering.

Example 9

Flow Cytometer Based Sorting and Isolation of Abeta-28 Plaque Particles

As performed earlier for isolation Abeta-42 plaque particles, AD serum sample incubated with Abeta-28 oligomers/aggregates were stained with Thioflavin dye and the resulting sample was used for Flow sorting. Unlike cholesterol particles, the fluorescence dot blot (FIG. 9C) shows only a single fraction of abeta particles population that was marked for sorting and isolation. The isolated Abeta-28 plaque particles were used for Mass spectroscopy analysis.

Thus, FIG. 9 shows a flow cytometer based sorting and isolation of Abeta-28 plaque particles. 9A shows acquisition blot displays detection of plaque particles in both side scattering (y-axis) and forward scattering (x-axis); 9B shows gating of fluorescence positive plaque particles population for sorting (x-axis 520 nm; y-axis 560 nm) and 9C shows acquisition dot blot displays sorting and isolation of gated fluorescence Abeta-28 plaque particles population. FSC refers to Forward scattering and SSC refers to side scattering.

Example 10

Flow Cytometer Based Sorting and Isolation of Tau Plaque Particles

In addition to Abeta peptides, Tau peptides are second major amyloid peptides found to be associated with amyloid plaques and implicated in the pathogenesis of AD related dementia (Bloom G S, 2014; Mathis Calif. et al, 2012). Hence, it was of interest to examine and compare the composition of serum derived Tau plaque particles. As described in the examples 8 and 9, AD serum samples incubated with Tau oligomer/aggregates were stained with Thioflavin S dye and the resulting samples were used for Flow sorting. As shown in FIGS. 10 A and B, the fluorescence Tau particles were gated for sorting. FIG. 10C shows isolated Tau plaque particles.

Figure 10A:
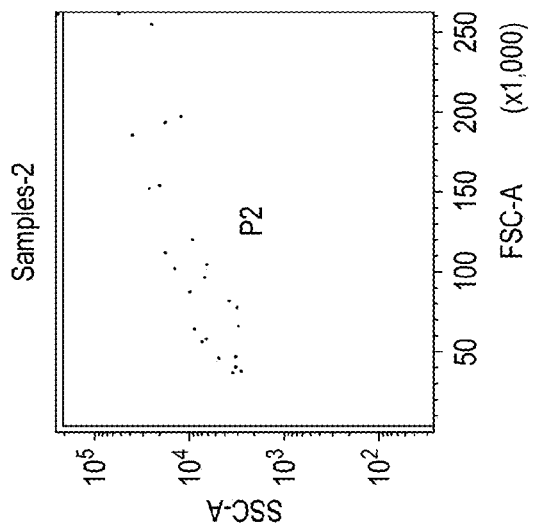
FIGS. 10A, 10B and 10C represents a flow cytometer based sorting and isolation of Tau (275-305) plaque particles.
Figure 10B:
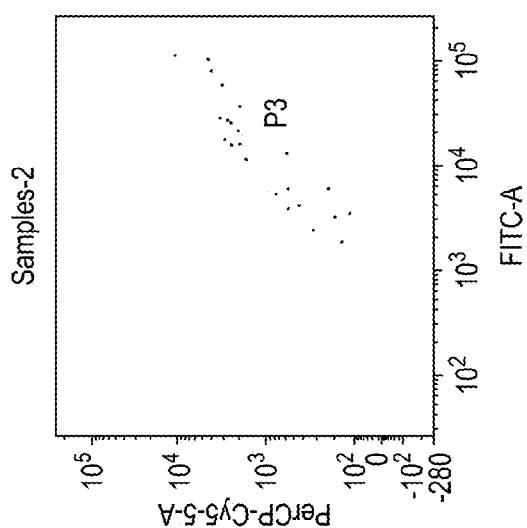
Figure 10C:
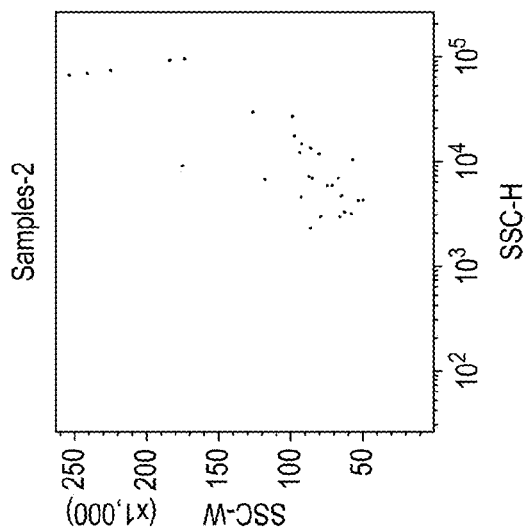

FIGS. 10A, 10 B and 10 C shows a flow cytometer based sorting and isolation of Tau (275-305) plaque particles. 10A shows acquisition dot blot showing detection of plaque particles in both side scattering (y-axis) and forward scattering (x-axis); 10B shows gating of fluorescence plaque particles population selected for sorting (x-axis 520 nm; y-axis 560 nm) and 10C shows sorting and isolation of gated fluorescence population of (275-305) plaque particles. FSC refers to forward scattering and SSC refers to side scattering.

Example 11

Figure 11C:
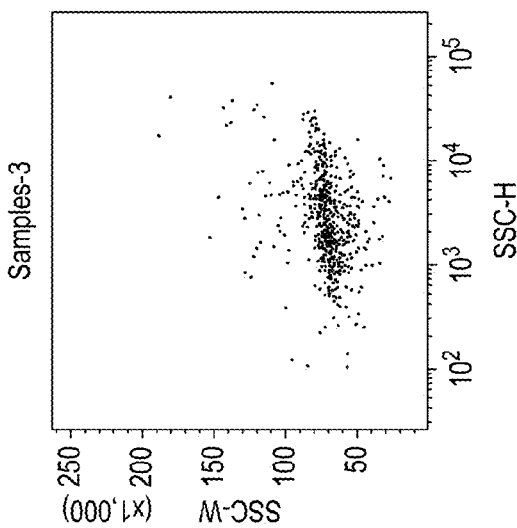
FIGS. 11a, 11B and 11C represents a flow cytometer based sorting and isolation of alpha-synuclein plaque particles.
Figure 11B:
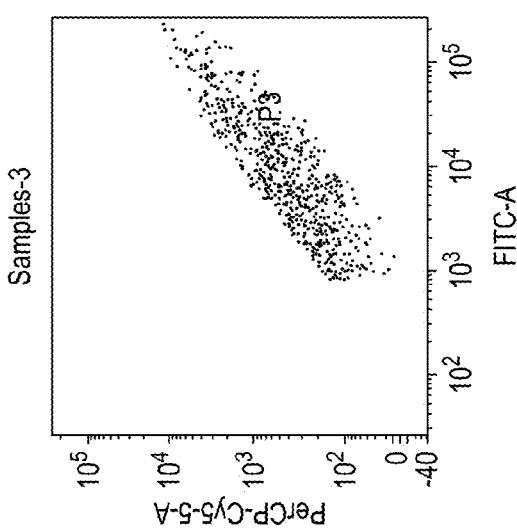
Figure 11A:
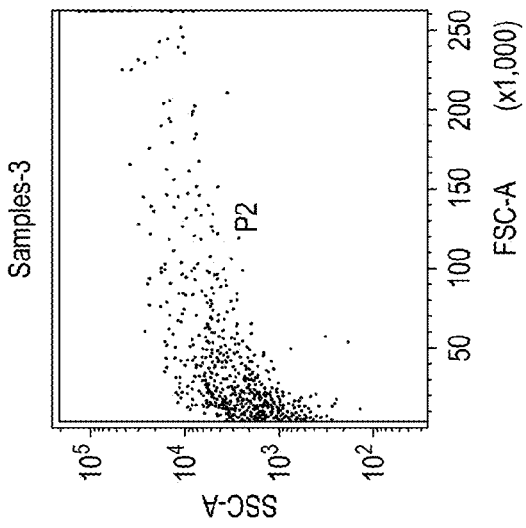
Figure 12A:
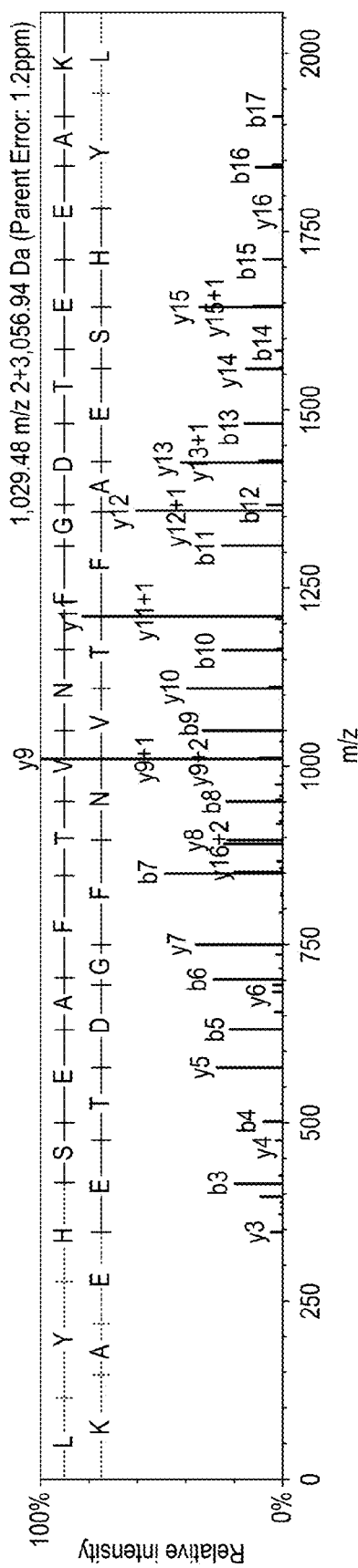
FIGS. 12A, 12B, 12C, 12D and 12E represents a mass spectrum data generated to deduce peptide sequences.
Figure 12B:
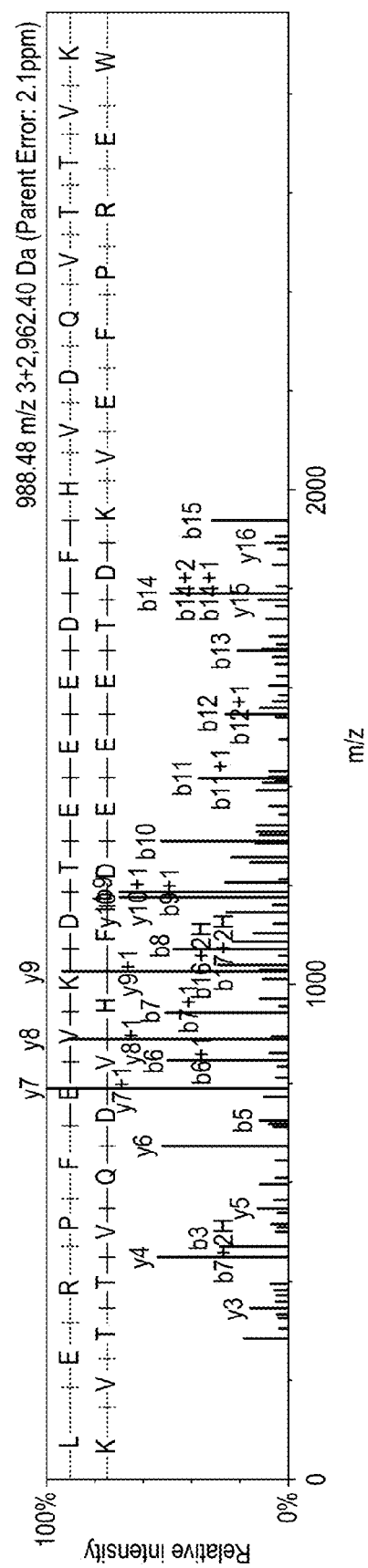
Figure 12C:
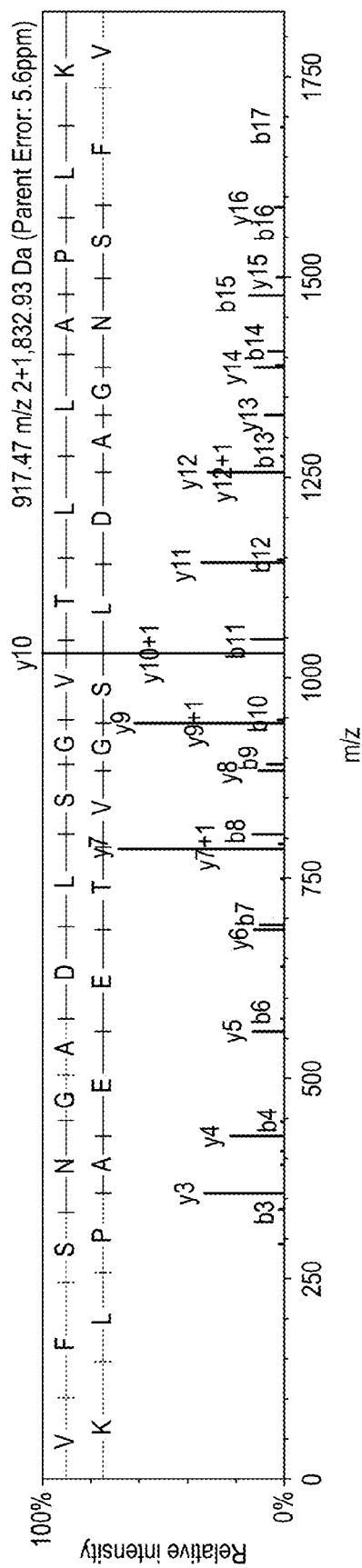
Figure 12D:
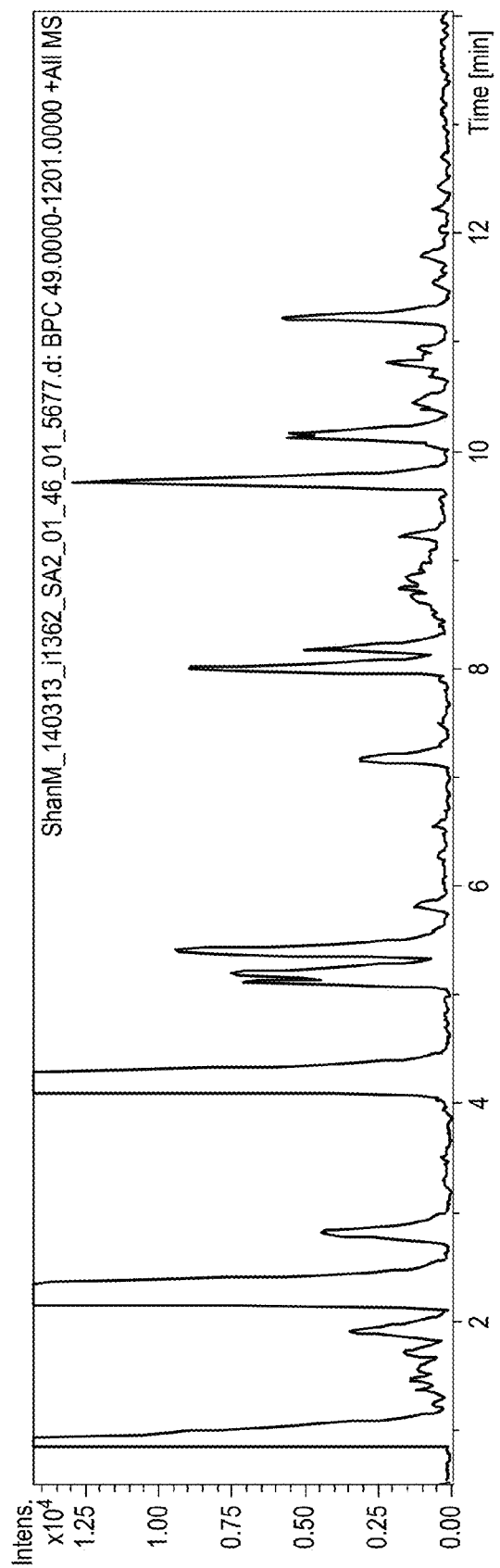
Figure 12E:
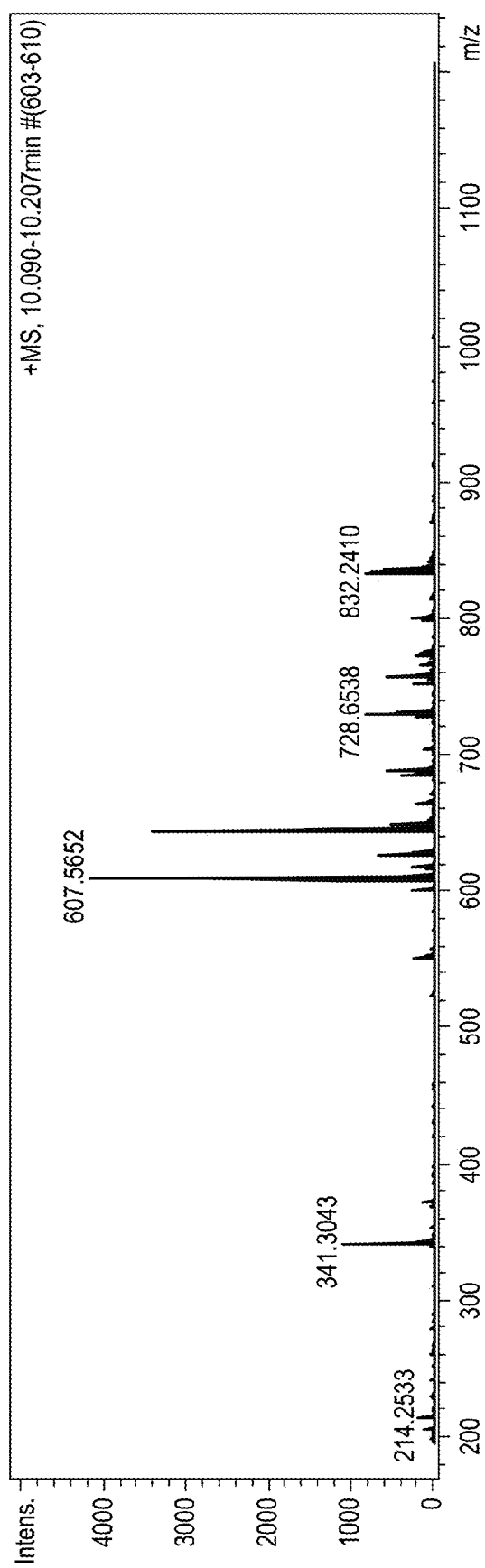
Figure 13A:
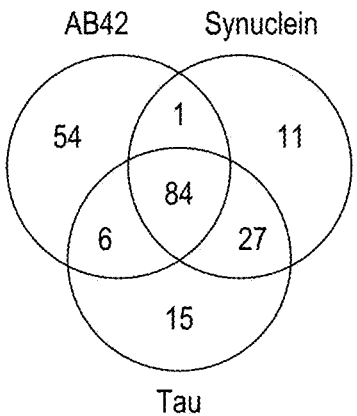
FIGS. 13A, 13B, 13C and 13D represents comparative analysis of common and specific proteins identified in plaque particles.
Figure 13B:
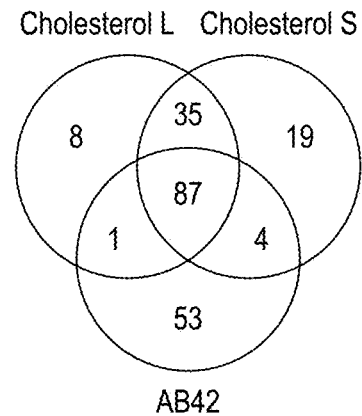
Figure 13C:
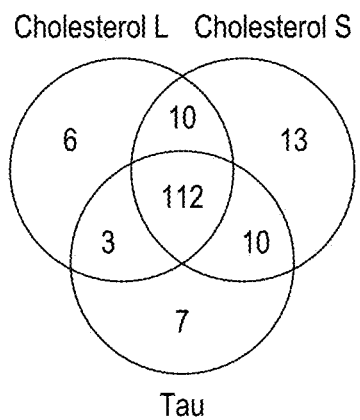
Figure 13D:
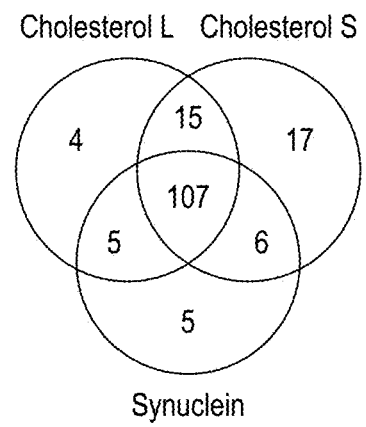

Flow Cytometer Based Sorting and Isolation of Alpha-Synuclein Plaque Particles Similar to Abeta and Tau peptides, alpha-synuclein is another major amyloid protein implicated in the development of Parkinson disease. These amyloid peptides and their aggregates often found co-accumulated in the cerebral regions thus contributing to the development of amyloid related neurodegenerative disorders (Hashimoto M, 1999). In the next step Flow sorting experiments were carried out to isolate alpha-synuclein plaque particles. As performed with other amyloid peptides, alpha-synuclein aggregates were incubated with AD serum samples and after staining with Thioflavin S dye the samples were used for Flow sorting. FIGS. 11A and 11B shows detection and gating of fluorescent alpha-synuclein plaque particles and FIG. 11C shows isolated plaque particles used for Mass spec analysis.

FIG. 11 shows a flow cytometer based sorting and isolation of alpha-synuclein plaque particles. 11A shows an acquisition dot blot showing detection of plaque particles in both side scattering (y-axis) and forward scattering (x-axis) acquisition blot; 11B shows a gating of fluorescence plaque particles population selected for sorting (x-axis 520 nm; y-axis 560 nm) and 11C shows sorting and isolation of gated fluorescence population of alpha-synuclein plaque particles. FSC refers to forward scattering and SSC refers to side scattering.

Example 12

Mass Spectroscopy Based Proteomics for Identification of Proteins in Plaque Particles The plaque particles isolated were used for identifying their composition by proteomics, glycomics, lipidomics and metabolomics approaches. For proteomics analysis, approximately 2000 particles of Abeta-42, Tau, alpha-synuclein, cholesterol L (High density cholesterol particles) and cholesterol S (Low density cholesterol particles) were taken. After trypsin digestion, purified peptide fragments were used for MS/MS analysis to generate peptide spectrum. Approximately 13778 peptide mass spectrums obtained were used for database search to identify the related proteins. Database search was carried out as described in the method section 4. Similarly, mass spec based lipidomics showed a number of lipid molecules present in the plaque particles. A few examples of Mass spectroscopy generated peptide spectrum and lipid chromatogram/spectrum are shown in FIG. 12.

FIG. 12 shows examples of Mass Spectrum data generated to deduce peptide sequences and lipid molecules. 12A shows a spectrum displays mass/charge (x-axis) and relative intensity of each peak (y-axis) the amino acid sequences of the peptide (LYHSEAFTVNFGDTEEAK) is shown at the top; 12B shows a spectrum displays mass/charge (x-axis)

and relative intensity of each peak (y-axis) the amino acid sequences of the peptide (Seq ID [[#]] NO: 8) (WERPFE-VKDTEEEDFHVDQVTTVK) is shown at the top and 12C shows a spectrum displays mass/charge (x-axis) and relative intensity of each peak (y-axis) the amino acid sequences of the peptide (Seq ID[[#]] NO: 9) (VFSNGADLSGVTEE-APLK) is shown at the top. 12D shows base peak chromatogram indicating number of lipid molecules in the plaque particles with (y-axis) displaying relative intensity of each peak and (x-axis) different fractions eluted over the time. 12E displays full scan mass spectra for identification of different lipids with (y-axis) displaying relative intensity of each spectrum and (x-axis) displaying mass/charge.

The database search of peptide spectrum obtained for all plaque particles revealed approximately 236 serum proteins in 188 clusters. The name of the proteins and their accession numbers are listed in Table 2. Further, analysis of the semi-quantitative binding profile of identified proteins showed that Abeta-42, cholesterol, Tau and alpha-synuclein particles have different levels of affinities to the proteins. It is important to note that some of these proteins are expected to present in the serum samples of normal subjects. However, under pathological conditions expression of these proteins might vary and they undergo post-translational modifications such as aberrant glycolylation, phophorylation, oxidation etc. Together, these factros contributing to pathogenesis of plaque related diseases including atherosclerosis and amyloidosis. These results strongly suggest that a wide range of proteins interplay in the plaque formation and their qualitative and quantitative analysis will greatly aid in the diagnosis, drug discovery and drug developments. Mass spectroscopy based measuring of expression of these proteins by multiple reaction monitoring (MRM) approach will further help to identify disease specific biomarkers in plaque development.

Example 14

Database of Proteins Identified in the Plaque Particles and Semi-Quantitative Analysis of their Binding Affinity Table 2 shows database of proteins identified for Abeta-42, High Density cholesterol (Chl Large), Low density cholesterol (Chl small), alpha-synuclein and Tau plaque particles. Higher numbers in the semi-quantitative columns refers to stronger affinity of a particular protein and lower the number refers to weaker affinity of the protein to the plaque particles.

TABLE 2

'Plaqueproteome' Database showing proteins associated with test plaque particles.

| Proteins identified from plaque particles Protein name | Semi-quantitative analysis of proteins binding to different plaque particles | | | | | Pub Med Database Protein Accession # |
|---|---|---|---|---|---|---|
| | Abeta-42 | Chl Large | Chl small | Synuclein | Tau | |
| 1. Serum albumin | 199 | 340 | 320 | 398 | 281 | sp|P02768 |
| 2. Cluster of Complement C3 | 63 | 73 | 67 | 71 | 85 | sp|P01024 |
| 3. Complement C3 | 63 | 73 | 67 | 71 | 85 | sp|P01024 |
| 4. Serotransferrin | 46 | 66 | 73 | 78 | 48 | sp|P02787 |
| 5. Apolipoprotein B-100 | 62 | 47 | 51 | 42 | 65 | sp|P04114 |
| 6. Cluster of Ig gamma-1 chain C region | 23 | 57 | 63 | 56 | 37 | sp|P01857 |
| 7. Ig gamma-1 chain C region | 12 | 41 | 51 | 44 | 27 | sp|P01857 |
| 8. Ig gamma-2 chain C region | 11 | 12 | 14 | 10 | 11 | sp|P01859 |
| 9. Ig gamma-3 chain C region | 11 | 15 | 11 | 14 | 13 | sp|P01860 |
| 10. Cluster of Alpha-2-macroglobulin | 32 | 43 | 43 | 44 | 45 | sp|P01023 |
| 11. Alpha-2-macroglobulin | 32 | 43 | 43 | 44 | 45 | sp|P01023 |
| 12. Pregnancy zone protein | 4 | 0 | 2 | 0 | 0 | sp|P20742 |
| 13. Cluster of Complement C4-B | 32 | 44 | 36 | 37 | 52 | sp|P0C0L5 |
| 14. Complement C4-B | 32 | 44 | 35 | 37 | 52 | sp|P0C0L5 |
| 15. Complement C4-A | 28 | 44 | 36 | 37 | 50 | sp|P0C0L4 |
| 16. Cluster of Keratin, type II cytoskeletal 2 epidermal | 171 | 14 | 20 | 3 | 24 | sp|P35908 |
| 17. Cluster of Alpha-1-antitrypsin | 28 | 22 | 21 | 20 | 28 | sp|P01009 |
| 18. Alpha-1-antitrypsin | 28 | 22 | 21 | 20 | 28 | sp|P01009 |
| 19. Ig kappa chain C region | 11 | 17 | 21 | 15 | 15 | sp|P01834 |
| 20. Apolipoprotein A-I | 19 | 21 | 21 | 18 | 14 | sp|P02647 |
| 21. Cluster of Haptoglobin | 25 | 29 | 31 | 24 | 26 | sp|P00738 |
| 22. Haptoglobin | 23 | 27 | 29 | 22 | 24 | sp|P00738 |
| 23. Isoform 2 of Haptoglobin-related protein | 11 | 15 | 12 | 14 | 11 | sp|P00739-2 |
| 24. Ceruloplasmin | 9 | 20 | 22 | 21 | 20 | sp|P00450 |
| 25. Isoform 3 of Fibronectin | 9 | 25 | 19 | 16 | 23 | sp|P02751-3 |
| 26. Cluster of Complement factor H | 4 | 13 | 15 | 10 | 11 | sp|P08603 |
| 27. Complement factor H | 4 | 13 | 15 | 10 | 11 | sp|P08603 |

TABLE 2-continued

'Plaqueproteome' Database showing proteins associated with test plaque particles.

| Proteins identified from plaque particles Protein name | Semi-quantitative analysis of proteins binding to different plaque particles | | | | | Pub Med Database Protein Accession # |
|---|---|---|---|---|---|---|
| | Abeta-42 | Ch1 Large | Ch1 small | Synuclein | Tau | |
| 28. Cluster of Ig alpha-1 chain C region | 9 | 10 | 9 | 12 | 12 | sp\|P01876 |
| 29. Ig alpha-1 chain C region | 9 | 10 | 8 | 11 | 12 | sp\|P01876 |
| 30. Ig alpha-2 chain C region | 7 | 9 | 6 | 10 | 10 | sp\|P01877 |
| 31. Plasminogen | 7 | 11 | 9 | 7 | 13 | sp\|P00747 |
| 32. Vitamin D-binding protein | 12 | 21 | 18 | 17 | 19 | sp\|P02774 |
| 33. Hemopexin | 11 | 22 | 16 | 18 | 16 | sp\|P02790 |
| 34. Transthyretin | 14 | 25 | 21 | 23 | 13 | sp\|P02766 |
| 35. Cluster of Ig mu chain C region | 5 | 10 | 10 | 9 | 11 | sp\|P01871 |
| 36. Ig mu chain C region | 5 | 10 | 10 | 8 | 10 | sp\|P01871 |
| 37. Ig mu heavy chain disease protein | 0 | 8 | 6 | 6 | 6 | sp\|P04220 |
| 38. Inter-alpha-trypsin inhibitor heavy chain H2 | 9 | 10 | 12 | 13 | 14 | sp\|P19823 |
| 39. Cluster of Inter-alpha-trypsin inhibitor heavy chain H4 | 2 | 20 | 13 | 12 | 15 | sp\|Q14624 |
| 40. Inter-alpha-trypsin inhibitor heavy chain H4 | 2 | 20 | 13 | 12 | 15 | sp\|Q14624 |
| 41. Isoform 2 of Inter-alpha-trypsin inhibitor heavy chain H4 | 2 | 20 | 13 | 12 | 15 | sp\|Q14624-2 |
| 42. Complement factor B | 12 | 9 | 14 | 10 | 13 | sp\|P00751 |
| 43. Cluster of Ig lambda-2 chain C regions | 9 | 5 | 9 | 8 | 11 | sp\|P0CG05 |
| 44. Ig lambda-2 chain C regions | 9 | 5 | 7 | 8 | 10 | sp\|P0CG05 |
| 45. Immunoglobulin lambda-like polypeptide 5 | 9 | 5 | 7 | 8 | 11 | sp\|B9A064 |
| 46. Ig lambda-7 chain C region | 2 | 3 | 2 | 4 | 3 | sp\|A0M8Q6 |
| 47. Ig lambda-6 chain C region | 5 | 3 | 3 | 6 | 5 | sp\|P0CF74 |
| 48. Prothrombin | 4 | 16 | 19 | 11 | 23 | sp\|P00734 |
| 49. Alpha-1-antichymotrypsin | 11 | 14 | 11 | 20 | 16 | sp\|P01011 |
| 50. Gelsolin | 2 | 8 | 9 | 6 | 9 | sp\|P06396 |
| 51. Cluster of Kininogen-1 | 0 | 4 | 8 | 6 | 1 | sp\|P01042 |
| 52. Kininogen-1 | 0 | 3 | 7 | 4 | 1 | sp\|P01042 |
| 53. Isoform LMW of Kininogen-1 | 0 | 4 | 8 | 6 | 1 | sp\|P01042-2 |
| 54. Antithrombin-III | 5 | 8 | 6 | 9 | 6 | sp\|P01008 |
| 55. Apolipoprotein A-IV | 5 | 8 | 9 | 7 | 10 | sp\|P06727 |
| 56. Alpha-2-HS-glycoprotein | 2 | 9 | 11 | 10 | 10 | sp\|P02765 |
| 57. Alpha-1B-glycoprotein | 4 | 7 | 7 | 11 | 6 | sp\|P04217 |
| 58. Afamin | 2 | 6 | 6 | 6 | 3 | sp\|P43652 |
| 59. Beta-2-glycoprotein 1 | 4 | 6 | 6 | 7 | 5 | sp\|P02749 |
| 60. Histidine-rich glycoprotein | 7 | 10 | 9 | 9 | 12 | sp\|P04196 |
| 61. Inter-alpha-trypsin inhibitor heavy chain H1 | 7 | 11 | 7 | 10 | 18 | sp\|P19827 |
| 62. Plasma protease C1 inhibitor | 4 | 7 | 7 | 9 | 3 | sp\|P05155 |
| 63. Apolipoprotein E | 11 | 7 | 9 | 8 | 13 | sp\|P02649 |
| 64. Apolipoprotein A-II | 5 | 8 | 6 | 7 | 10 | sp\|P02652 |
| 65. Complement C5 | 0 | 5 | 3 | 4 | 1 | sp\|P01031 |
| 66. Serum paraoxonase/arylesterase | 2 | 5 | 6 | 7 | 3 | sp\|P27169 |
| 67. C4b-binding protein alpha chain | 0 | 8 | 8 | 7 | 1 | sp\|P04003 |
| 68. Angiotensinogen | 14 | 10 | 9 | 7 | 15 | sp\|P01019 |
| 69. CD5 antigen-like | 4 | 6 | 7 | 6 | 3 | sp\|O43866 |
| 70. Zinc-alpha-2-glycoprotein | 5 | 4 | 5 | 7 | 4 | sp\|P25311 |
| 71. Cluster of Desmoplakin | 12 | 0 | 0 | 0 | 0 | sp\|P15924 |
| 72. Alpha-1-acid glycoprotein 2 | 9 | 5 | 7 | 10 | 9 | sp\|P19652 |
| 73. Alpha-1-acid glycoprotein 1 | 12 | 9 | 8 | 7 | 11 | sp\|P02763 |
| 74. Cluster of Hemoglobin subunit beta | 4 | 3 | 2 | 5 | 3 | sp\|P68871 |
| 75. Hemoglobin subunit delta | 0 | 0 | 0 | 2 | 0 | sp\|P02042 |
| 76. Protein AMBP | 5 | 5 | 5 | 5 | 10 | sp\|P02760 |

TABLE 2-continued

'Plaqueproteome' Database showing proteins associated with test plaque particles.

| Proteins identified from plaque particles Protein name | Semi-quantitative analysis of proteins binding to different plaque particles | | | | | Pub Med Database Protein Accession # |
|---|---|---|---|---|---|---|
| | Abeta-42 | Chl Large | Chl small | Synuclein | Tau | |
| 77. Vitronectin | 4 | 4 | 2 | 4 | 4 | sp\|P04004 |
| 78. Alpha-2-antiplasmin | 0 | 6 | 3 | 5 | 5 | sp\|P08697 |
| 79. Hemoglobin subunit alpha | 2 | 4 | 5 | 5 | 5 | sp\|P69905 |
| 80. Complement C1r subcomponent | 0 | 2 | 4 | 3 | 4 | sp\|P00736 |
| 81. Isoform 2 of Clusterin | 4 | 6 | 4 | 7 | 5 | sp\|P10909-2 |
| 82. Cluster of Ig kappa chain V-III region | 2 | 4 | 4 | 7 | 4 | sp\|P01620 |
| 83. Plasma kallikrein | 0 | 1 | 3 | 0 | 3 | sp\|P03952 |
| 84. Complement component C7 | 0 | 4 | 6 | 1 | 4 | sp\|P10643 |
| 85. Cluster of Ig kappa chain V-IV region Len | 4 | 5 | 4 | 6 | 3 | sp\|P01625 |
| 86. Heparin cofactor 2 | 0 | 3 | 1 | 1 | 6 | sp\|P05546 |
| 87. Apolipoprotein D | 0 | 2 | 2 | 1 | 3 | sp\|P05090 |
| 88. Complement factor I | 0 | 4 | 3 | 4 | 3 | sp\|P05156 |
| 89. Corticosteroid-binding globulin | 0 | 2 | 3 | 1 | 1 | sp\|P08185 |
| 90. Pigment epithelium-derived factor | 5 | 4 | 3 | 4 | 4 | sp\|P36955 |
| 91. Ig gamma-4 chain C region | 7 | 7 | 11 | 8 | 11 | sp\|P01861 |
| 92. Complement component C6 | 0 | 1 | 1 | 3 | 1 | sp\|P13671 |
| 93. Cluster of Ig kappa chain V-I region DEE | 5 | 5 | 1 | 3 | 2 | sp\|P01597 |
| 94. Ig kappa chain V-I region DE | 5 | 5 | 1 | 3 | 2 | sp\|P01597 |
| 95. Ig kappa chain V-I region Mev | 0 | 1 | 1 | 0 | 0 | sp\|P01612 |
| 96. Ig kappa chain V-I region AU | 2 | 1 | 1 | 0 | 0 | sp\|P01594 |
| 97. Isoform 2 of Fibrinogen alpha chain | 0 | 0 | 1 | 0 | 1 | sp\|P02671-2 |
| 98. Cluster of Ig kappa chain V-II region TEW | 2 | 1 | 4 | 2 | 1 | sp\|P01617 |
| 99. Complement C1s subcomponent | 0 | 3 | 1 | 1 | 2 | sp\|P09871 |
| 100. Cluster of Ig heavy chain V-III region TEI | 7 | 5 | 6 | 4 | 5 | sp\|P01777 |
| 101. Ig heavy chain V-III region TEI | 5 | 4 | 5 | 3 | 4 | sp\|P01777 |
| 102. Ig heavy chain V-III region BRO | 7 | 5 | 6 | 4 | 5 | sp\|P01766 |
| 103. Kallistatin | 0 | 1 | 0 | 0 | 1 | sp\|P29622 |
| 104. Retinol-binding protein 4 | 0 | 2 | 2 | 2 | 2 | sp\|P02753 |
| 105. Isoform 2 of Apolipoprotein L1 | 0 | 1 | 1 | 0 | 2 | sp\|O14791-2 |
| 106. Insulin-like growth factor-binding protein complex | 0 | 1 | 1 | 0 | 1 | sp\|P35858 |
| 107. Ig heavy chain V-III region Gal | 2 | 0 | 1 | 2 | 4 | sp\|P01781 |
| 108. Carboxypeptidase N subunit 2 | 0 | 0 | 1 | 2 | 1 | sp\|P22792 |
| 109. Lumican | 0 | 4 | 3 | 0 | 0 | sp\|P51884 |
| 110. Immunoglobulin J chain | 0 | 1 | 1 | 2 | 1 | sp\|P01591 |
| 111. Apolipoprotein C-III | 4 | 4 | 4 | 1 | 5 | sp\|P02656 |
| 112. Leucine-rich alpha-2-glycoprotein | 2 | 2 | 3 | 2 | 1 | sp\|P02750 |
| 113. Complement component C8 beta chain | 0 | 1 | 2 | 0 | 2 | sp\|P07358 |
| 114. Coagulation factor XII | 0 | 0 | 0 | 1 | 1 | sp\|P00748 |
| 115. Complement component C8 gamma chain | 0 | 0 | 1 | 2 | 2 | sp\|P07360 |
| 116. Serum amyloid A-4 protein | 2 | 1 | 1 | 1 | 4 | sp\|P35542 |
| 117. Complement C2 | 0 | 0 | 1 | 0 | 0 | sp\|P06681 |
| 118. Complement component C8 alpha chain | 0 | 3 | 2 | 0 | 0 | sp\|P07357 |

TABLE 2-continued

'Plaqueproteome' Database showing proteins associated with test plaque particles.

| Proteins identified from plaque particles Protein name | Semi-quantitative analysis of proteins binding to different plaque particles | | | | | Pub Med Database Protein Accession # |
|---|---|---|---|---|---|---|
| | Abeta-42 | Chl Large | Chl small | Synuclein | Tau | |
| 119. Isoform 2 of N-acetylmuramoyl-L-alanine amidase | 0 | 4 | 1 | 2 | 5 | sp\|Q96PD5-2 |
| 120. Serum amyloid P-component | 5 | 1 | 1 | 0 | 2 | sp\|P02743 |
| 121. Ig lambda chain V-III region LOI | 2 | 1 | 1 | 2 | 1 | sp\|P80748 |
| 122. Ig kappa chain V-III region VG | 0 | 1 | 0 | 1 | 0 | sp\|P04433 |
| 123. Complement C1q subcomponent subunit B | 0 | 1 | 0 | 2 | 2 | sp\|P02746 |
| 124. Desmoglein-1 | 5 | 0 | 0 | 0 | 0 | sp\|Q02413 |
| 125. Filaggrin | 2 | 0 | 0 | 0 | 0 | sp\|P20930 |
| 126. Vitamin K-dependent protein S | 0 | 0 | 1 | 0 | 0 | sp\|P07225 |
| 127. Ig heavy chain V-III region BUT | 2 | 1 | 1 | 1 | 1 | sp\|P01767 |
| 128. Apolipoprotein C-II | 0 | 0 | 1 | 1 | 0 | sp\|P02655 |
| 129. Platelet basic protein | 0 | 0 | 0 | 1 | 2 | sp\|P02775 |
| 130. Ig lambda chain V-III region | 0 | 1 | 1 | 2 | 2 | sp\|P01714 |
| 131. Thyroxine-binding globulin | 2 | 0 | 1 | 0 | 1 | sp\|P05543 |
| 132. Ig kappa chain V-III region NG9 | 0 | 2 | 1 | 2 | 3 | sp\|P01621 |
| 133. Ig kappa chain V-I region Ni | 5 | 2 | 2 | 2 | 3 | sp\|P01613 |
| 134. Cluster of Ig kappa chain V-I region HK102 | 5 | 1 | 1 | 1 | 1 | sp\|P01602 |
| 135. Ig kappa chain V-I region HK102 | 5 | 1 | 1 | 1 | 1 | sp\|P01602 |
| 136. Ig kappa chain V-I region CAR | 5 | 1 | 1 | 1 | 1 | sp\|P01596 |
| 137. Lactotransferrin | 5 | 0 | 0 | 0 | 0 | sp\|P02788 |
| 138. Isoform Short of Heterogeneous nuclear ribonucleoprotein | 4 | 0 | 0 | 0 | 0 | sp\|Q00839-2 |
| 139. Apolipoprotein C-I | 2 | 1 | 1 | 0 | 1 | sp\|P02654 |
| 140. Hornerin | 2 | 0 | 0 | 0 | 1 | sp\|Q86YZ3 |
| 141. Phosphatidylinositol-glycan-specific phospholipase D | 0 | 1 | 1 | 0 | 2 | sp\|P80108 |
| 142. Tetranectin | 0 | 0 | 1 | 0 | 0 | sp\|P05452 |
| 143. Filaggrin-2 | 4 | 0 | 0 | 0 | 0 | sp\|Q5D862 |
| 144. Isoform 2 of Ficolin-3 | 0 | 0 | 0 | 1 | 0 | sp\|O75636-2 |
| 145. Cluster of Ig heavy chain V-III region VH26 | 7 | 2 | 3 | 1 | 3 | sp\|P01764 |
| 146. Ig heavy chain V-III region VH26 | 7 | 2 | 3 | 1 | 3 | sp\|P01764 |
| 147. Ig heavy chain V-III region TIL | 5 | 0 | 2 | 0 | 2 | sp\|P01765 |
| 148. Complement C1q subcomponent subunit C | 0 | 1 | 1 | 1 | 2 | sp\|P02747 |
| 149. Cluster of Platelet factor 4 | 2 | 1 | 0 | 1 | 1 | sp\|P02776 |
| 150. Platelet factor 4 | 2 | 1 | 0 | 1 | 1 | sp\|P02776 |
| 151. Platelet factor 4 variant | 0 | 1 | 0 | 1 | 0 | sp\|P10720 |
| 152. Cluster of Actin, cytoplasmic 1 | 0 | 3 | 0 | 0 | 0 | sp\|P60709 |
| 153. Actin, cytoplasmic 1 | 0 | 3 | 0 | 0 | 0 | sp\|P60709 |
| 154. Complement component C9 | 0 | 1 | 1 | 1 | 0 | sp\|P02748 |
| 155. Junction plakoglobin | 2 | 0 | 0 | 0 | 0 | sp\|P14923 |
| 156. Ig heavy chain V-III region WEA | 2 | 1 | 1 | 1 | 1 | sp\|P01763 |
| 157. Cluster of Isoform B of Fibulin-1 | 0 | 3 | 3 | 1 | 0 | sp\|P23142-3 |
| 158. Isoform B of Fibulin-1 | 0 | 3 | 3 | 1 | 0 | sp\|P23142-3 |
| 159. Isoform C of Fibulin-1 | 0 | 1 | 2 | 1 | 0 | sp\|P23142-4 |

TABLE 2-continued

'Plaqueproteome' Database showing proteins associated with test plaque particles.

| Proteins identified from plaque particles Protein name | Semi-quantitative analysis of proteins binding to different plaque particles | | | | | Pub Med Database Protein Accession # |
|---|---|---|---|---|---|---|
| | Abeta-42 | Chl Large | Chl small | Synuclein | Tau | |
| 160. Protein S100-A7 | 2 | 0 | 0 | 0 | 0 | sp\|P31151 |
| 161. Isoform 2 of Glycogen synthase kinase-3 | 4 | 0 | 0 | 0 | 0 | sp\|P49841-2 |
| 162. Cluster of Nucleolar RNA helicase 2 | 2 | 0 | 0 | 0 | 0 | sp\|Q9NR30 |
| 163. Nucleolin OS = Homo sapiens GN = NCL PE = 1 SV = 3 | 4 | 0 | 0 | 0 | 0 | sp\|P19338 |
| 164. Protein-glutamine gamma-glutamyltransferase E | 2 | 0 | 0 | 0 | 0 | sp\|Q08188 |
| 165. Ig heavy chain V-III region JON | 0 | 0 | 1 | 1 | 1 | sp\|P01780 |
| 166. Ig kappa chain V-I region Wes | 2 | 2 | 1 | 2 | 2 | sp\|P01611 |
| 167. Cluster of Interleukin enhancer-binding factor 3 | 4 | 0 | 0 | 0 | 0 | sp\|Q12906 |
| 168. Interleukin enhancer-binding factor 3 | 4 | 0 | 0 | 0 | 0 | sp\|Q12906 |
| 169. Isoform 2 of Spermatid perinuclear RNA-binding protein | 2 | 0 | 0 | 0 | 0 | sp\|Q96SI9-2 |
| 170. Isoform 2 of Annexin A2 | 2 | 0 | 0 | 0 | 0 | sp\|P07355-2 |
| 171. Isoform 1B of Desmocollin-1 | 4 | 0 | 0 | 0 | 0 | sp\|Q08554-2 |
| 172. Coagulation factor XIII B chain | 0 | 0 | 1 | 0 | 0 | sp\|P05160 |
| 173. Cluster of Ig heavy chain V-III region NIE | 4 | 2 | 3 | 1 | 0 | sp\|P01770 |
| 174. Ig heavy chain V-III region NIE | 0 | 1 | 1 | 1 | 0 | sp\|P01770 |
| 175. Ig heavy chain V-III region TUR | 4 | 2 | 3 | 1 | 0 | sp\|P01779 |
| 176. Cluster of Histone H1.2 | 2 | 0 | 0 | 0 | 0 | sp\|P16403 |
| 177. Histone H1.2 | 2 | 0 | 0 | 0 | 0 | sp\|P16403 |
| 178. Histone H1.3 | 2 | 0 | 0 | 0 | 0 | sp\|P16402 |
| 179. Isoform 2 of Arginase-1 | 2 | 0 | 0 | 0 | 0 | sp\|P05089-2 |
| 180. Caspase-14 | 5 | 0 | 0 | 0 | 0 | sp\|P31944 |
| 181. Ig lambda chain V-IV region Hil | 0 | 0 | 1 | 0 | 1 | sp\|P01717 |
| 182. Ig kappa chain V-I region BAN | 2 | 2 | 1 | 1 | 2 | sp\|P04430 |
| 183. Cathepsin D | 5 | 0 | 0 | 0 | 0 | sp\|P07339 |
| 184. Complement factor H-related protein 1 | 0 | 2 | 1 | 0 | 1 | sp\|Q03591 |
| 185. Galectin-3-binding protein | 0 | 1 | 0 | 0 | 0 | sp\|Q08380 |
| 186. Ig heavy chain V-I region HG3 | 2 | 1 | 1 | 2 | 1 | sp\|P01743 |
| 187. Heterogeneous nuclear ribonucleoprotein R | 2 | 0 | 0 | 0 | 0 | sp\|O43390 |
| 188. Lysozyme C | 4 | 0 | 0 | 0 | 0 | sp\|P61626 |
| 189. RNA polymerase-associated protein CTR9 | 2 | 0 | 0 | 0 | 0 | sp\|Q6PD62 |
| 190. 40S ribosomal protein S8 | 4 | 0 | 0 | 0 | 0 | sp\|P62241 |
| 191. Isoform APP639 of Amyloid beta A4 protein | 4 | 0 | 0 | 0 | 0 | sp\|P05067-10 |
| 192. Phosphatidylcholine-sterol acyltransferase | 0 | 1 | 0 | 1 | 0 | sp\|P04180 |
| 193. Apolipoprotein F | 0 | 0 | 1 | 2 | 1 | sp\|Q13790 |
| 194. Coagulation factor X | 0 | 0 | 1 | 0 | 0 | sp\|P00742 |
| 195. Glyceraldehyde-3-phosphate dehydrogenase | 5 | 0 | 0 | 0 | 0 | sp\|P04406 |
| 196. Parafibromin | 2 | 0 | 0 | 0 | 0 | sp\|Q6P1J9 |
| 197. Isoform 2 of C4b-binding protein beta chain | 0 | 0 | 1 | 0 | 0 | sp\|P20851-2 |
| 198. Cluster of Nuclease-sensitive element-binding protein 1 | 4 | 0 | 0 | 0 | 0 | sp\|P67809 |

TABLE 2-continued

'Plaqueproteome' Database showing proteins associated with test plaque particles.

| Proteins identified from plaque particles Protein name | Semi-quantitative analysis of proteins binding to different plaque particles | | | | | Pub Med Database Protein Accession # |
|---|---|---|---|---|---|---|
| | Abeta-42 | Chl Large | Chl small | Synuclein | Tau | |
| 199. Nuclease-sensitive element-binding protein 1 | 4 | 0 | 0 | 0 | 0 | sp\|P67809 |
| 200. Isoform Tau-G of Microtubule-associated protein tau | 0 | 0 | 0 | 0 | 2 | sp\|P10636-9 |
| 201. Tubulin alpha-1A chain | 0 | 3 | 0 | 0 | 0 | sp\|Q71U36 |
| 202. Serpin B3 | 2 | 0 | 0 | 0 | 0 | sp\|P29508 |
| 203. Immunoglobulin lambda-like polypeptide 1 | 0 | 0 | 1 | 0 | 0 | sp\|P15814 |
| 204. Ig kappa chain V-III region IARC/BL41 | 0 | 0 | 1 | 0 | 2 | sp\|P06311 |
| 205. Thioredoxin | 2 | 0 | 0 | 0 | 0 | sp\|P10599 |
| 206. Ig kappa chain V-III region POM | 0 | 1 | 1 | 0 | 2 | sp\|P01624 |
| 207. Cluster of Histone H2A type 1-B/E | 0 | 0 | 1 | 0 | 0 | sp\|P04908 |
| 208. Isoform 2 of Histone H2A.J | 0 | 0 | 1 | 0 | 0 | sp\|Q9BTM1-2 |
| 209. Cluster of RNA polymerase II-associated factor 1 homolog | 2 | 0 | 0 | 0 | 0 | sp\|Q8N7H5 |
| 210. 40S ribosomal protein S4, X | 4 | 0 | 0 | 0 | 0 | sp\|P62701 |
| 211. Isoform 2 of Protein SET | 4 | 0 | 0 | 0 | 0 | sp\|Q01105-2 |
| 212. Isoform 2 of RNA-binding protein 39 | 2 | 0 | 0 | 0 | 0 | sp\|Q14498-2 |
| 213. Selenoprotein P | 0 | 0 | 0 | 1 | 0 | sp\|P49908 |
| 214. Isoform 2 of Nucleophosmin | 4 | 0 | 0 | 0 | 0 | sp\|P06748-2 |
| 215. 60S ribosomal protein L10 | 2 | 0 | 0 | 0 | 0 | sp\|P27635 |
| 216. Ig heavy chain V-III region WA | 4 | 1 | 2 | 0 | 1 | sp\|P01776 |
| 217. Dermcidin | 2 | 0 | 0 | 0 | 0 | sp\|P81605 |
| 218. 60S ribosomal protein L18 | 2 | 0 | 0 | 0 | 0 | sp\|Q07020 |
| 219. Serpin B12 | 2 | 0 | 0 | 0 | 0 | sp\|Q96P63 |
| 220. Carboxypeptidase N catalytic chain | 0 | 0 | 0 | 0 | 1 | sp\|P15169 |
| 221. Tubulin beta-4B chain | 0 | 0 | 0 | 0 | 5 | sp\|P68371 |
| 222. Putative tubulin beta chain-like protein | 0 | 0 | 0 | 0 | 6 | sp\|A6NKZ8 |
| 223. Peroxiredoxin-1 | 5 | 0 | 0 | 0 | 0 | sp\|Q06830 |
| 224. Myosin-6 | 17 | 0 | 0 | 0 | 0 | sp\|P13533 |
| 225. Myosin-13 | 17 | 0 | 0 | 0 | 0 | sp\|Q9UKX3 |
| 226. Myosin-1 | 22 | 0 | 0 | 0 | 0 | sp\|P12882 |
| 227. Isoform MBP-1 of Alpha-enolase | 7 | 0 | 0 | 0 | 0 | sp\|P06733-2 |
| 228. Tropomyosin alpha-3 chain | 5 | 0 | 0 | 0 | 0 | sp\|P06753-3 |
| 229. Guanine deaminase | 5 | 0 | 0 | 0 | 0 | sp\|Q9Y2T3-3 |
| 230. Nucleoside diphosphate kinase A | 5 | 0 | 0 | 4 | 0 | sp\|P15531-2 |
| 231. GTP-binding nuclear protein | 5 | 0 | 0 | 0 | 0 | sp\|P62826 |
| 232. Catalase | 12 | 0 | 0 | 0 | 0 | sp\|P04040 |
| 233. Apolipoprotein M | 18 | 0 | 0 | 0 | 0 | sp\|O95445 |
| 234. Actin, cytoplasmic 1 | 49 | 0 | 0 | 27 | 0 | sp\|P60709 |
| 235. POTE ankyrin domain family member E | 18 | 0 | 0 | 18 | 0 | sp\|Q6S8J3 |
| 236. Spectrin | 12 | 5 | 5 | 24 | 6 | |

Table 2 shows database of "plaqueproteome" identified for Abeta-42, High Density cholesterol (Chl Large), Low density cholesterol (Chl small), alpha-synuclein and Tau plaque particles. The database of biomarkers described herein will be used to select one or more biomarkers for developing assays for selective identification of each plaque particles. Such selective plaque test assays will be used for diagnosis, drug screening and drug development purposes.

Example 13

Comparative Analysis of Identified Peptides and Proteins in Different Plaque Particles Interestingly, comparative analysis of proteins identified in all plaque particles reveals that a large number of proteins, shown in the intersection of Venn diagram, are overlapped in all plaque particles (FIG. 13A, 13B, 13C, 13D). In addition, number of specific proteins identified for all plaque particles are shown in the left, right and bottom of Venn diagram. Significantly, it was observed that abeta-42 plaque particles generated in the AD serum samples contain more specific proteins compared to age-matched control together, these results suggest that proteins identified in this study might play key role in modulating "plaque formation system". Previously, multiple clinical and proteomics studies been carried out identify biomarkers from whole serum or plasma samples of atherosclerosis and AD (Yuasa Y et al, 2014; Wang Q et al, 2005; Sui X et al, 2014; Minjarez B et al, 2014). Conversely, the method described herein, instead of analyzing total proteins of bio-fluids, is more specific in identifying molecules or biomarkers that interplay in the plaque formation system.

FIG. 13 shows a comaparative analysis of common and specific proteins identified in plaque particles. 13A shows a Venn diagram showing number of proteins identified in all three amyloid plaque particles (intersection of three sets) and specific proteins identified (shown in left, right and bottom of three sets) in a particular type of plaque particle. 13B shows a Venn diagram showing number of proteins shared (intersection of three sets) among cholesterol and a beta 42plaque particles and specific proteins identified (shown in left, right and bottom of three sets) in a particular type of plaque particles. Cholesterol L refers to High density cholesterol paticles and Cholesterol S refers to Low density cholesterol particles. C, diagram showing number of proteins identified among choelerol, and Tau plaque particles (intersection of three sets) and specific proteins identified (shown in left, right and bottom of three sets) in a particular type of plaque particle. D, Venn diagram showing number of proteins shared (intersection of three sets) among cholesterol and alpha-synuclein plaque particles and specific proteins identified (shown in left, right and bottom of three sets) in a particular type of plaque particles.

Example 14

Figure 14:
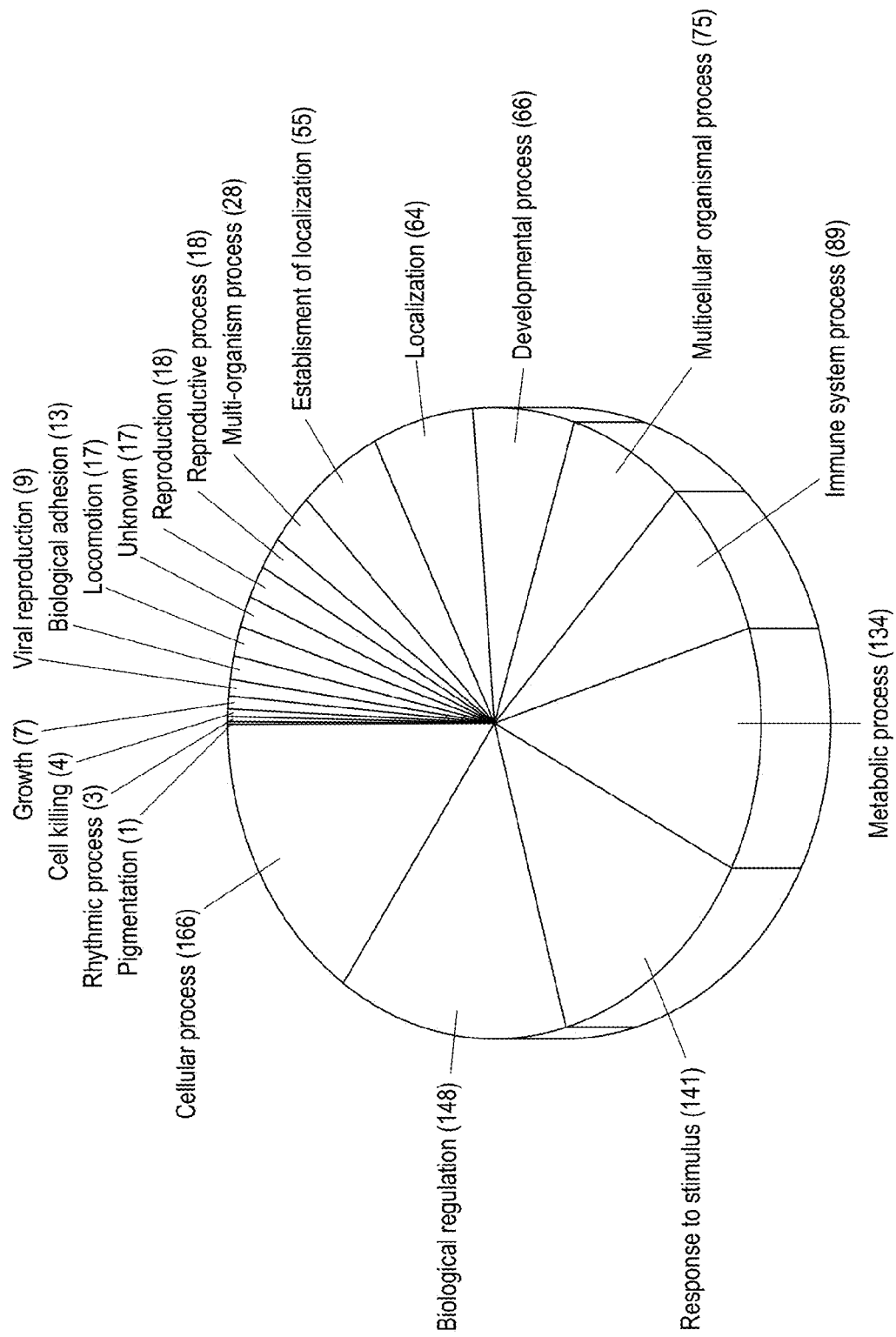
FIG. 14 represents a pie chart showing clusters of proteins identified for the plaque particles formation and their link to multiple biochemical pathways.

Analysis of Protein Clusters and their Role in Multiple Biochemical and Cellular Pathways The proteins identified in various plaque particles are known to be involved in the function of multiple biochemical pathways. The database analysis of these proteins showed that they are associated with 188 clusters (FIG. 14) with five major clusters among them are metabolic, immune, complement, proteases and apolipoprotein pathways. Under normal conditions these proteins play key roles in the functions of these biochemical pathways. However, under pathological conditions expression of these proteins may be up or down regulated leading to biochemical and cellular dysfunctions causing serious plaque related medical conditions such as myocardial infarction and dementia. To probe the post-translational glycosylation of proteins, the search of plaqueproteome database described here revealed Nex and O=Hex NAc modification in multiple proteins.

Example 15

Identification of Plaque Specific Antibodies for Therapeutic and Diagnosis Applications Human immune system plays key role in modulating origin and progression of atherosclerotic and amyloid plaques. Antibodies are involved in the endogenous clearance of pathogenic atherosclerotic or amyloid aggregates/oligomers and defective clearance of plaque aggregates leads to accelerated accumulation of plaques in the arteries. Accordingly, the search of our 'plaqueproteomics" database helped us to identify the following plaque specific antibodies and their fragments.

TABLE 3

Abeta-42 specific antibody sequences involved in the Abeta plaque particles formation:

| Sequence Number | Name | Sequence |
| --- | --- | --- |
| SEQ ID NO: 10 | Lambda chain-7 C region | GQPKAAPSVTLFPPSSEELQANKATLVCLVSDF YPGAVTVAWKADGSPVKVGVETTKPSKQSNN KYAASSYLSLTPEQWKSHRSYSCRVTHEGSVEK TVAPAECS |
| SEQ ID NO: 11 | Kappa chain V-III region VH | MEAPAQLLFLLLWLPDTTREIVMTQSPPTLSLSP GERVTLSCRASQSVSSSYLTWYQQKPGQAPRLL IYGASTRATSIPARFSGSGSGTDFTLTISSLQPEDF AVYYCQQDHNLP |
| SEQ ID NO: 12 | Heavy chain V-III region | EVQLLESGGGLVQPGGSLRLSCAASGFTFSRVLSS WVRQAPGKGLEWVSGRLNASSNLHFAVSAQGRF TISRNDSKNTLYLQMLSLQAZBTALYYCARLLSVY AVAFDVWGQGTKVS |
| SEQ ID NO: 13 | Ig gamma-2 chain C region | ASTKGPSVFPLAPCSRSTSESTAALGCLVKDYFPEP VTVSWNSGALTSGVHTFPAVLQSSGLYSLSSVVTV PSSNFGTQTYTCNVDHKPSNTKVDKTVERKCCVE CPPCPAPPVAGPSVFLFPPKPKDTLMISRTPEVTCV VVDVSHEDPEVQFNWYVDGVEVHNAKTKPREEQ FNSTFRVVSVLTVVHQDWLNGKEYKCKVSNKGLP APIEKTISKTKGQPREPQVYTLPPSREEMTKNQVSL TCLVKGFYPSDISVEWESNGQPENNYKTTPPMLDS DGSFFLYSKLTVDKSRWQQGNVFSCSVMHEALHN HYTQKSLSLSPGK |

TABLE 3-continued

Abeta-42 specific antibody sequences involved in the Abeta plaque particles formation:

| Sequence Number | Name | Sequence |
|---|---|---|
| SEQ ID NO: 14 | Ig gamma-1 chain C region | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEVT CVVVDVSHEDPEVKFNWYVDGVEVHNAKTKPRE EQYNSTYRVVSVLTVLHQDWLNGKEYKCKVSNK ALPAPIEKTISKAKGQPREPQVYTLPPSRDELTKNQ VSLTCLVKGFYPSDIAVEWESNGQPENNYKTTPPV LDSDGSFFLYSKLTVDKSRWQQGNVFSCSVMHEA LHNHYTQKSLSLSPGK |

TABLE 4

Tau specific antibody sequences involved in the Tau plaque particles formation:

| Sequence Number | Name | Sequence |
|---|---|---|
| SEQ ID NO: 15 | Ig kappa chain region V-III* | EIVLTQSPGTLSLSPGERATLSCRAALLSSRGYLAWY QQKPGQAPRLLMYGASSRATGIPDRFSGSGSGTDFTL TISRLEPEDFAVYYCQQYGSSPRSFGQGTKVEIKR |
| SEQ ID NO: 16 | Ig kappa chain region V-III (2) | EIVLTQSPGTLSLSPGERATLSCRASQSVSNSFLAWYQ QKPGQAPRLLIYVASSRATGIPDRFSGSGSGTDFTLTIS RLEPEDFAVYYCQQYGSSPSTFGQGTVELKR |

*Ig kappa chain region V-III with unique peptide sequences determining Tau specific binding.

TABLE 5

Alpha-synuclein specific antibody sequences involved in the plaque particles formation:

| Sequence Number | Name | Sequence |
|---|---|---|
| SEQ ID NO: 17 | Ig kappa chain region V-I | DVQMTQSPSSLSAVGDRVIITCRASQSSV DYLNWYQQKPGKAPKLLIFDTSNLQSGV PSRFSGGRSGTDFTLTISSLQPDDFATYYC QQSYTNPEVTFGGGTTVDIKR |
| SEQ ID NO: 18 | Ig kappa chain V-II region | DVVMTQSPLFPVTLGEPASIQCRSSQSLVYB GBTYLBWYLQKPGSPELLIYLSSYRDSGVPD RLSDSGSGTDFTLKITRVQAEDVGVYYCMQ ATZSPYTFGQGTKLZIKR |

TABLE 6

Cholesterol (High density and low density) specific antibody sequences involved in the cholesterol plaque particles formation:

| Sequence Number | Name | Sequence |
|---|---|---|
| SEQ ID NO: 19 | Ig kappa V-I region | DIQMTQSPSTLSASVGDRVAIRTCRASQNI SSWLAWYQQKPGKAPKVLIYKSSSLESGV PSRFSGSGSGTDTDFTLTISSLZPBBFATYYC QQYNTFFTGPGTVDIKR |
| SEQ ID NO: 20 | Heavy chain V-III region | EVQLLESGGGLVQPGGSLRLSCAASGFSFS TDAMYWVRQAPGKGLEWVAWKYQEASN SHFADTVNRGFTISRNDSKNTLYLQMNRLE AZBTAVYYCARFRQPFVQFFDVFGQGTLVT |

TABLE 6-continued

Cholesterol (High density and low density) specific antibody sequences involved in the cholesterol plaque particles formation:

| Sequence Number | Name | Sequence |
|---|---|---|
| SEQ ID NO: 21 | Ig heavy chain V-III region | QVKLVQAGGGVVQPGRSLRLSCIASGFTF SNHGMHWVRQAPGKGLEWVAVIWYNGS RTYYGDSVKGRFTISRNDNSKRTLYMZMN SLRTEDTAVYYCARDPDILTAFSFDYWGQG VLVTVSS |

The human antibody fragments identified here are suitable for insertion/modification into the gene encoding full length human antibody and the resulting constructs can be used to express respective functional antibodies. These novel antibodies can be successfully used as therapeutics to treat plaque related diseases in affected patients of atherosclerosis and AD. In addition, they can be used as lead molecules for further optimization to improve their specificity and efficacy. The resulting optimized antibodies have multiple applications including use as therapeutics and for diagnosis of plaque related diseases.

In conclusion, the flow cytometer based plaque array method in combination with Mass spectroscopy has been successfully used to identify compositions of various plaque particles that are related cardiovascular and neurodegenerative diseases. The ex vivo plaque formation model system described herein could be used to discover novel therapeutic molecules that modulate the process of atherosclerotic and amyloid plaque particles formation. In addition, these biomarkers identified have multiple applications including understanding mechanism of plaque development, clinical diagnosis of plaque related diseases, patient profiling, personalized medicine, companion diagnosis, pre-clinical studies in animals, drug discovery and drug developments.

The invention has been described using exemplary preferred embodiment. However, for those skilled in this field, the preferred embodiment can be easily adapted and modified to suit additional applications without departing from the spirit and scope of this invention. Thus, it is to be understood that the scope of the invention is not limited to the disclosed embodiment. On the contrary, it is intended to cover various modifications and similar arrangements based upon the same operating principle. The scope of the claims, therefore, should be accorded the broadest interpretations so as to encompass all such modifications and similar arrangements. Accordingly, the specification and drawings are to be regarded in an illustrative rather than a restrictive sense.

What is claimed is:

1. An in vitro method of synthesizing an insoluble plaque particle, comprising:
   a) preparing a soluble amyloid plaque aggregate;
   b) contacting a serum sample from a subject with the soluble amyloid plaque aggregate to form the insoluble plaque particle that is detectable in the serum sample of a patient;
   c) detecting and quantifying the insoluble plaque particle using flow cytometer that do not detect the soluble amyloid plaque aggregate in the serum sample of a patient;
   d) isolating the insoluble plaque particle; and
   e) analyzing the insoluble plaque particle to identify composition using mass spectrometry for stratifying the specific insoluble plaque particle.

2. An in vitro method of screening for a candidate agent to treat a plaque associated disease, comprising:
 a) preparing a soluble amyloid plaque aggregate in vitro wherein the plaque aggregate is linked to a detectable signal;
 b) mixing a serum sample from a subject with the soluble amyloid plaque aggregate to form an insoluble plaque particle in an accelerated form outside the body;
 c) adding a candidate agent to the serum sample before and after mixing with the soluble amyloid plaque aggregate to form the insoluble plaque particle;
 d) isolating and detecting the insoluble plaque particle with and without the candidate agent using flow cytometer and collecting an isolated sample of the plaque particle for each serum sample;
 e) analyzing and identifying a biomolecule in the isolated sample of the insoluble plaque particle using mass spectrometry; and
 f) analyzing and identifying of the biomolecule identified in the plaque particle isolated from the serum sample not in contact with the candidate agent to the sample of insoluble plaque particle to screen the candidate agent as an anti-plaque agent.

3. The method of claim 2, wherein the candidate agent is an Abeta-42 antibody.

\* \* \* \* \*